US008445288B2

(12) United States Patent
Sorensen et al.

(10) Patent No.: US 8,445,288 B2
(45) Date of Patent: May 21, 2013

(54) SOLID-PHASE DETECTION OF TERMINAL MONOSACCHARIDES CLEAVED FROM GLYCOSYLATED SUBSTRATES

(75) Inventors: Mads Detlef Sorensen, Farum (DK); Rita Martins, Lund (SE); Ole Hindsgaul, Copenhagen (DK)

(73) Assignee: Merck Patent GmbH, Darmstadt (DE)

( * ) Notice: Subject to any disclaimer, the term of this patent is extended or adjusted under 35 U.S.C. 154(b) by 881 days.

(21) Appl. No.: 12/373,331

(22) PCT Filed: Jul. 10, 2007

(86) PCT No.: PCT/DK2007/000352
§ 371 (c)(1),
(2), (4) Date: Oct. 7, 2009

(87) PCT Pub. No.: WO2008/006373
PCT Pub. Date: Jan. 17, 2008

(65) Prior Publication Data
US 2010/0047828 A1   Feb. 25, 2010

Related U.S. Application Data

(60) Provisional application No. 60/807,145, filed on Jul. 12, 2006.

(30) Foreign Application Priority Data

Jul. 12, 2006 (DK) .................................. 2006 00969

(51) Int. Cl.
*G01N 33/00* (2006.01)
*C12Q 1/54* (2006.01)

(52) U.S. Cl.
USPC ............... 436/94; 436/95; 436/164; 436/166; 436/172; 435/7.1; 435/14

(58) Field of Classification Search ........................ None
See application file for complete search history.

(56) References Cited

U.S. PATENT DOCUMENTS
2005/0191761 A1    9/2005  Heiss et al.

FOREIGN PATENT DOCUMENTS
| WO | WO 90/04596 A1 | 5/1990 |
| WO | WO 92/19974 A1 | 11/1992 |
| WO | WO 2004/096817 A1 | 11/2004 |
| WO | WO 2006/084461 A1 | 8/2006 |

OTHER PUBLICATIONS

James et al. "Novel Saccharide-Photoinduced Electron Transfer Sensors Based on the Interaction of Boronic Acid and Amine", 1. Am. Chem. Soc. 1995, v. 117, pp. 8982-8987.*

* cited by examiner

*Primary Examiner* — Yelena G Gakh
(74) *Attorney, Agent, or Firm* — Millen, White, Zelano & Branigan, P.C.

(57) ABSTRACT

The present invention relates to a novel method for analysing carbohydrates. The invention is in particular useful in detecting a terminal monosaccharide which may be released from a glycosylated substrate for example using an exoglucosidase. After relase from the glycosylated substrate the terminal monosaccharide may be captured on a solid support, incubated with a boronate detection agent and detected by aid of the boronate detection agent. The methods of the invention are useful for a variety of purposes including sequencing of carbohydrates, wherein exoglycosidases with predetermined specificity are employed for the release.

10 Claims, 13 Drawing Sheets a) Phenyl boronic acid derviatives:

b) Phenyl boronic acid derviatives with an o-aminomethyl moiety:

c) Phenyl boronic acid derviatives with a substituted o-aminomethyl moiety:

d) Phenyl boronic acid derviatives bearing an electronegative substituent:

e) Pyridine boronic acid derivatives f) Phenyl boronic acid derviatives with a sulfonamide or sulfone substitutent g) Phenyl boronic acid derviatives bearing an o-hydroxymethyl group h) Phenyl boronic acid derviatives bearing a substituted o-hydroxymethyl group i) Phenyl boronic acid derviatives bearing a quaternary amine substituent j) Multiple aryl boronic acid derviatives k) boronic acid derviatives of 5-membererd ring heterocyles l) Phenyl boronic acid derviatives with fused rings:

acetic anhydride benzoic anhydride trichloroacetic anhydride trifluoroacetic anhydride α,α'-dibromo-o-xylene benzoic acid NHS-ester Capture Beads Fluorescent hydroxymethyl-boronate (1)

Fluorescent nitro-boronate (2)

SOLID-PHASE DETECTION OF TERMINAL MONOSACCHARIDES CLEAVED FROM GLYCOSYLATED SUBSTRATES

This application claims the benefit of the filing date of U.S. Provisional Application Ser. No. 60/807,145 filed Jul. 12, 2006.

FIELD OF INVENTION

The present invention relates to the field of carbohydrate analysis. In particular, the invention relates to new methods for identifying the terminal sugar-residues of carbohydrate chains, and for sequencing carbohydrates, such as carbohydrates found in biological samples. Thus, in one aspect the invention relates to the field of carbohydrate detection and structural characterisation.

BACKGROUND OF THE INVENTION

Carbohydrates exist in many forms in nature. In animals including man, examples include free reducing sugars in solution (such as the monosaccharide glucose in serum), free oligosaccharides in solution (such as the disaccharide lactose in milk), they can be attached to peptides or proteins through covalent linkages to a variety of amino acids (such as asparagine, serine, threonine and others), covalently attached to lipids such as ceramide (as in gangliosides) or attached to membrane anchors via phosphatidylinositols. Sugars are also found attached to many small molecules including some involved in metabolism, such as glucuronides. In the above examples, the length of the sugar chains can vary from one to over 100 sugar residues.

In lower organisms, including bacteria and plants, an even wider array of structures exists. The surface of bacterial cells can be covered by sugar polymers that are thousands of residues long, which can act as antigens in the detection of bacteria and as vaccines. Sugars are an integral part of bacterial cell walls. The sugars can themselves be antibiotics (such as the aminoglycoside antibiotics, for example streptomycin), or can be found as essential components of antibiotics (such as erythromycin and vancomycin), as enzyme inhibitors (as in Acarbose) or as anti-cancer agents (such as for example calicheamycin).

One area of particular interest is the structure of the carbohydrate chains (glycans) found attached to glycoproteins and glycolipids. The glycosylation pattern of glycoproteins has been shown to be important for their biological functions, including their bioavailablity, their targeting, and have even been directly correlated with the metastatic potential of tumor cells. The glycosylation pattern of human serum transferrin, for example, is being used as a diagnostic test for a series of genetic diseases termed Carbohydrate-Deficient Glycosylation Syndromes. Specific glycolipid sequences have been shown to be involved in neuronal development and cell surface signalling, in diabetes, and are accumulated in certain specific metabolic diseases such as Tay-Sachs, for which they are diagnostic.

The linkages between the sugar residues in the oligosaccharides and polysaccharides described above can have either the alpha or beta configurations, and the glycans can be multiply branched. The diversity of structures possible for glycan chains is therefore enormous and their structural characterization is therefore inherently complex. There is therefore a strong interest in methods for the detection, structural characterization, identification, quantitation, and chemical/enzymatic manipulation of carbohydrate and glycan structures, in research, in diagnostics, in monitoring the glycosylation of recombinant glycoproteins and in the development of new pharmaceutical agents. In this last context, the degree of terminal galactosylation and sialyation of the glycan chains of recombinant glycoprotein drugs such as erythreopoetin is critically important for its effectiveness.

Several methods are in current use for the analysis for carbohydrate structures, and these have recently been reviewed. Underivatized oligosaccharides and glycolipids can be analyzed by NMR-spectroscopy, by mass-spectrometry, and by chromatography. For the much larger glycoproteins, mass spectrometry provides more limited information but analysis of their proteolytic digests, i.e. glycopeptides, has been extensively used. Indirect structural information about underivatized oligosaccharides can also be deduced from their abilities to interact with carbohydrate-binding proteins such as lectins, antibodies or enzymes.

Carbohydrates themselves have no characteristic chromophores, only N-acetyl groups, so monitoring their separation by optical or spectroscopic detection is not commonly used. Pulsed amperometric detection of the polyols has however been an important technique for detection in chromatography. This technique has also been applied to the detection and identification of monosaccharides in solution.

The most widely used method for high-sensitivity detection of carbohydrates has been the labeling of the reducing ends (lactols, tautomers of hydroxyaldehydes and hydroxyketones) with either radioactive or fluorescent TAGs. Both chemical and enzymatic methods have been described that cleave carbohydrates from glycoproteins and glycolipids, permitting the generation of the required reducing sugars from glycoproteins (including monosaccharides released by exo-glycosidases or acid-hydrolysis), glycolipds and other glycoconjugates. Most commonly, such reducing sugars are reacted with amino-containing derivatives of fluorescent molecules under conditions of reductive amination: i.e., where the initially formed imines (C=N) are reduced to amines (CH—NH) to produce a stable linkage. In most cases, the labeling reactions have been performed in solution using a large excess of labeling agent. This requires separation of the excess labeling agent and its by-products prior to or during analysis. Other TAGs of utility in mass-spectrometry have been added in the same manner, by either amination or reductive amination, the detection then being performed by the mass-spectrometer.

Once the label has been added to permit specific detection, the carbohydrates (including monosaccharides) described above can subsequently be subjected to separation and detection/quantification. If specific glycosidases act on the tagged carbohydrates, they can cleave one or more sugar residues resulting in a change in chromatographic or electrophoretic mobility, as detected by, for example, a fluorescence detector in HPLC, CE or by a change in their mobility in SDS-PAGE, or a change in their mass as detected by a change in m/z value in a mass-spectrometer. Arrays of enzymes have been used to provide a higher throughput analysis.

Below a short overview of prior art is given:

Gao et al. 2003 reviews suitable techniques for derivatisation of carbohydrates in solution. In solution carbohydrates may be derivatised by reductive amination. In general, —$NH_2$ groups of amines may react with aldehyde or ketone group of reducing sugars, thereby producing compounds of —C=N structure. Such compounds may further be reduced for example by $NaCNBH_3$. Gao et al., 2003 does not disclose the capture or detection of terminal monosaccharides released from glycosylated substrates.

U.S. Pat. No. 5,100,778 describes a method for oligosaccharide sequencing comprising placing an identifying label on the reducing terminal residue of an oligosaccharide, dividing into a plurality of separate portions, treating each portion with for example specific glycosidases, pooling product and analysing the pools obtained. The document does not describe immobilised terminal monosaccharides.

U.S. Pat. No. 4,419,444 describes methods for chemically binding organic compounds containing carbohydrate residues to a support bearing reactive —$NH_2$ groups. The methods involve either the periodate oxidation of carbohydrate diols to produce reactive aldehydes by cleaving of C—C bonds in the carbohydrate or oxidation of —$CH_2OH$ groups to —CHO groups enzymatically. Both oxidations will result in alteration of the structure of the carbohydrate. The reactive aldehydes can be immobilised by reaction with the —$NH_2$ groups. After immobilisation of the carbohydrate containing compound a reduction step (for example using $NaBH_4$) may be performed to increase stability. The document does not describe the immobilization of a single monosaccharide after cleavage from a carbohydrate-containing compound. Furthermore, the chemical nature of the carbohydrate has been altered and this alteration may impair further modulations, such as specific enzymatic cleavage by glycosidases. The document also does not describe the addition of any chemical reagents to the immobilised carbohydrates that result in the addition of molecular structures to it.

WO92/719974 describes a method of sequencing oligosaccharides. The method involves immobilising oligosaccharides on a solid support and subsequent treatment with a variety of glycosidases. Prior to immoblisation, the oligosaccharide may be linked to a conjugate. The document does not describe modulation of immobilised terminal monosaccharides, nor indeed treatment with the tagged compounds of the present invention.

Lohse et al. ("Solid-Phase Oligosaccharide Tagging (SPOT): Validation on Glycolipid-Derived Structures", Angew. Chem. Int. Ed. 2006, 45, 4167-4172) disclose Solid-Phase Oligosaccharide Tagging on glycolipid-derived structures, however this article does not disclose cleavage of terminal monosaccharides from glycosylated substrates before analysis of the immobilised monosaccharides, nor indeed the use of the specific boronate compounds disclosed herein.

Various boronate compounds have been previously used for labelling and detecting carbohydrates in solution, such as disclosed in e.g. the following references:

"Boronic Acids: Preparation, Applications in Organic Synthesis and Medicine", ed. Dennis G. Hall, pub. Wiley-VCH, in particular in chapters 12 and 13 ("Boronic Acid-based receptors and sensors for saccharides" and "Biological and medicinal applications of boronic acids").

Yan et al., "Boronolectins and Fluorescent Boronolectins: An Examination of the Detailed Chemistry Issues Important for the Design", Medicinal Reseach Reviews, Vol. 25, No. 5, 490-520, 2005

Mulla et al., "3-Methoxycarbonyl-5-nitrophenyl boronic acid: high affinity diol recognition at neutral pH", Bioorganic & Medicinal Chemistry Letter 14 (2004) 25-27

Dowlut et al., "An Improved Class of Sugar-Binding Boronic Acids, Soluble and Capable of Complexing Glycosides in Neutral Water", J. Am. Chem. Soc. 2006, 128, 4226-7

Hoeg-Jensen., "Preparation and Screening of Diboronate Arrays for Identification of Carbohydrate Binders", QSAR Comb., Sci. 2004, 23

Boduroglu et al., "A colorimetric titration method for quantification of millimolar glucose in a pH 7.4 aqueous phosphate buffer", Bioorganic & Medicinal Chemistry Letter 15 (2005) 3974-3977

Davis et al., "Simple and Rapid Visual Sensing of Saccharides", Organic Letter, 1999 Vol. 1, No. 2, 331-334

He et al., "Chromophore Formation in Resorcinarene Solutions and the Visual detection of Mono- and Oligosaccharides", J. Am. Chem. Soc. 2003, 124, 5000-5009

Gray et al., "Specific sensing between inositol epimers by a bis(boronate)", Bioorganic & Medicinal Chemistry Letters 15 (2005) 5416-5418)

However, none of the above-mentioned compounds have been used to label and detect carbohydrates immobilised to a solid support, nor indeed terminal monosaccharides attached to a solid support.

The above sections describe the biological importance and complexity of glycans, and summarizes some benefits of attaching TAGs such as boronates to sugars, including monosaccharides, although not to immobilised terminal monosaccharides after cleavage from a carbohydrate-containing molecule. To date, such TAG attachment has only been performed in solution using large excesses of tagging agent (and often additional chemical agents such as reducing agents), and thus require time consuming and frequently difficult separation techniques to be applied before either detection or further manipulation. There is therefore a great need for simple methods that can allow easier carbohydrate sequencing through identification of a terminal monosaccharide, without the need for complex methods for separating reaction starting materials, reagents, by-products and sought after products. We describe herein such simple methods.

SUMMARY OF THE INVENTION

In solution monosaccharides are found primarily in cyclic forms. Thus, in solution aidohexoses are for example primarily present as pyranoses with a smaller fraction being present as furanoses. Only a very minor fraction is present as open chain aldehyde or hydrate (see for example Zhu et al., 2001, J. org. Chem, 66:6244-6251). Interestingly, Dowlut et al., 2006, J. Am. Chem. Soc, 128: 4226-4227 states that "no boronic acid unit has yet been demonstrated to bind to non-reducing sugars and glycosides" (p. 4226, $1^{st}$ col. I. 8-10). The document furthermore discloses a specific orthosubstituted aryl boronic acid which only binds to glycosides with an extremely low affinity ($K_a$ in the range of 22-34 $M^{-1}$). Accordingly, in solution in the absence of a reducing agent only a very minor fraction of monosaccharides are capable of interacting with boronates.

As is apparent from the above, the particular conformational structure of a sugar is very important for the ability to interact with boronic acid or boranates. The prior art does not describe or hint at whether immobilised sugars may adopt a conformation allowing binding of boronic acid or boronates. Interestingly, the present invention discloses that boronates may be useful in the detection of immobilised terminal monosaccharides. In fact the present invention discloses that immobilised terminal monosaccharides may even be visually detected using tagged boronates.

Thus, the present invention provides a method for analysis of a terminal monosaccharide on a glycosylated substrate, said method comprising the steps of:—
(i) detaching said monosaccharide from said glycosylated substrate, preferably using an exoglycosidase;
(ii) allowing said detached monosaccharide to covalently bind to a capture group on a solid support;

(iii) incubating said covalently bound monosaccharide with a detection agent with formula X:
TAG-R-Boronate
wherein TAG=a tag moiety capable of being detected
R=organic moiety
Boronate=a boronic acid moiety or ester thereof,
said boronate being attached to a carbon atom comprised in said R group;
(iv) allowing the detection agent to bind the monosaccharide
(v) detecting detection agent having bound to the monosaccharide.

Preferably, said detection agent has formula selected from: TAG-R—B(OH)$_2$, TAG-R—B(OH)(OR') or TAG-R—B(OR')(OR")
wherein R'and R" may be either aliphatic or aromatic and are optionally covalently attached to R.

The steps comprised in said method can be repeated at least once (as described further herein below), such as 1, 2, 3, 4, 5, 6, 7, 8, 9, 10 or more times, in order to allow efficient sequencing of monosaccharide(s) comprised in the glycosylated substrate. The method can also be carried out on different carbohydrate chains on the same glycosylated substrate, and/or repeated more than once.

The methods of the present invention may be applied to the detection, identification and quantitation of terminal glycosylation pattern of recombinant glycoproteins such as biopharmaceuticals, for example for identifying and quantifying terminal glycose residues that are present on glycosylated substrates such as glycoproteins, glycopeptides, glycolipids, polysaccharides and oligosaccharides. In particular, the method is shown to distinguish between terminally sialyated glycoproteins and terminally galactosylated glycoproteins.

Thus, the methods of the present invention may in one embodiment be used to identify particular glycosylation patterns associated with certain pathological conditions. Therefore, in a further aspect of the present invention is disclosed a method of diagnosis of a disease associated with abnormal glycoprotein glycosylation, comprising subjecting a sample of glycoproteins obtained from a patient to a method as disclosed herein.

The methods of the present invention may also be advantageously used to assay for bacterial contamination of products, thus in another aspect of the present invention is provided a method for monitoring for bacterial contamination of products, such as pharmaceutical products, comprising sujecting a sample of said product to one of the methods disclosed herein.

Further disclosed herein are detection agents suitable for use in the methods of the present invention, as well as covalent adducts formed between a monosaccharide and said detection agent(s). Furthermore, fluorescent compounds suitable for use in the detection agents according to the present invention are disclosed.

In another aspect of the present invention is disclosed a kit of parts suitable for using in the methods of the present invention, said kit of parts comprising at least one solid support, at least one capture group, and one or more of the detection agents disclosed herein.

f) Phenyl boronic acid derivatives bearing a sulfonamide or a sulfone substituent: S may be o, m or p to the boron X=alkyl, aryl, heteroaryl, substituted alkyl, substituted aryl, substituted heteroaryl, fused alkyl or heteroaryl ring, NR(R=H, alkyl, cycloalkyl, aryl, substituted alkyl, substituted cycloalkyl, substituted aryl)

Example: X=NHCH$_2$CO, TAG=Tetramethylrhodamine.

The free acid form of the boronate is shown, though esters are also implied.

Figure 7:
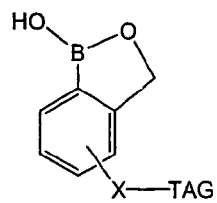
Figure 7:
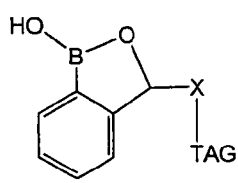
Figure 7:
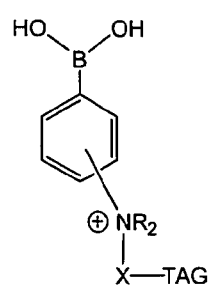

FIG. 7. Examples g-i of structures of TAG-R-Boronate M.

g) Phenyl boronic acid derivatives bearing an o-hydroxymethyl group:

X=alkyl, aryl, heteroaryl, substituted alkyl, substituted aryl, substituted heteroaryl, fused alkyl or heteroaryl ring, NH, O, S, CO, X-TAG substituent may be o, m or p to the boron Example: X=p (to CH$_2$)—NH, TAG=Tetramethylrhodamine (1);

h) Phenyl boronic acid derivatives bearing a substituted o-hydroxymethyl group:

X=alkyl, aryl, heteroaryl, substituted alkyl, substituted aryl, substituted heteroaryl, fused alkyl or heteroaryl ring, CO Example: X=CH$_2$CO, TAG=Tetramethylrhodamine;

i) Phenyl boronic acid derivatives bearing a quaternary ammonium substituent:

X=alkyl, aryl, heteroaryl, substituted alkyl, substituted aryl, substituted heteroaryl, fused alkyl or heteroaryl ring, R=H, alkyl cycloalkyl, aryl, substituted alkyl, substituted cycloalkyl, substituted aryl.

Example: R=CH$_2$CO, TAG=Tetramethylrhodamine.

The free acid form of the boronate is shown, though esters are also implied.

Figure 8:
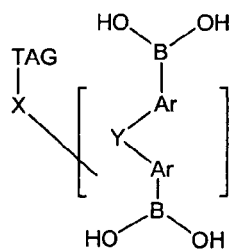
Figure 8:
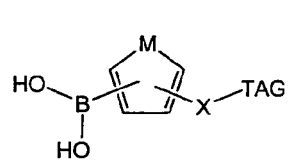
Figure 8:
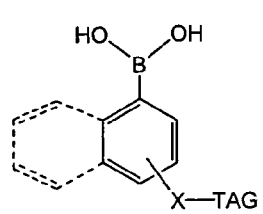

FIG. 8. Examples j-I of structures of TAG-R-Boronate M.

j) Derivatives with multiple aryl boronic acids;

X=alkyl, aryl, heteroaryl, substituted alkyl, substituted aryl, substituted heteroaryl, fused alkyl or heteroaryl ring, NH, O, S, CO Y=a linking moiety X-TAG substituent may be on the aryl groups or the linking moiety Example: Ar=phenyl, Y=m,m-CH$_2$ TAG=Tetramethylrhodamine;

k) Boronic acid derivatives of aromatic 5-membered ring heterocycles:

X=alkyl, aryl, heteroaryl, substituted alkyl, substituted aryl, substituted heteroaryl, fused alkyl or heteroaryl ring, NH, O, S, CO X-TAG and B(OH)$_2$ substituent may be o, m

M=N, O, S

Example: X=o (to M)-CO, TAG=Tetramethylrhodamine, m (to M)-B(OH)$_2$.

l) Phenyl boronic acid derivatives containing fused rings.

X=alkyl, aryl, heteroaryl, substituted alkyl, substituted aryl, substituted heteroaryl, fused alkyl or heteroaryl ring, NH, O, S, CO X-TAG substituent may be o, m or p to the boron Rings may be fused at any two adjacent positions Rings may be substituted Example: of an o-naphtalene derivative:

X=m-NH, TAG=Tetramethylrhodamine, fused ring=phenyl.

The free acid form of the boronate is shown, though esters are also implied.

Figure 9:
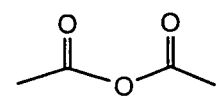
Figure 9:
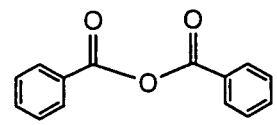
Figure 9:
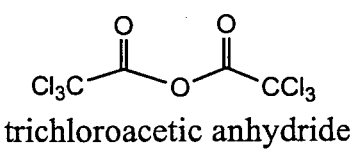
Figure 9:
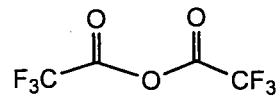
Figure 9:
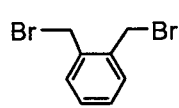
Figure 9:
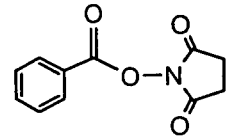

FIG. 9. Structures of some capping agents.

Figure 10:
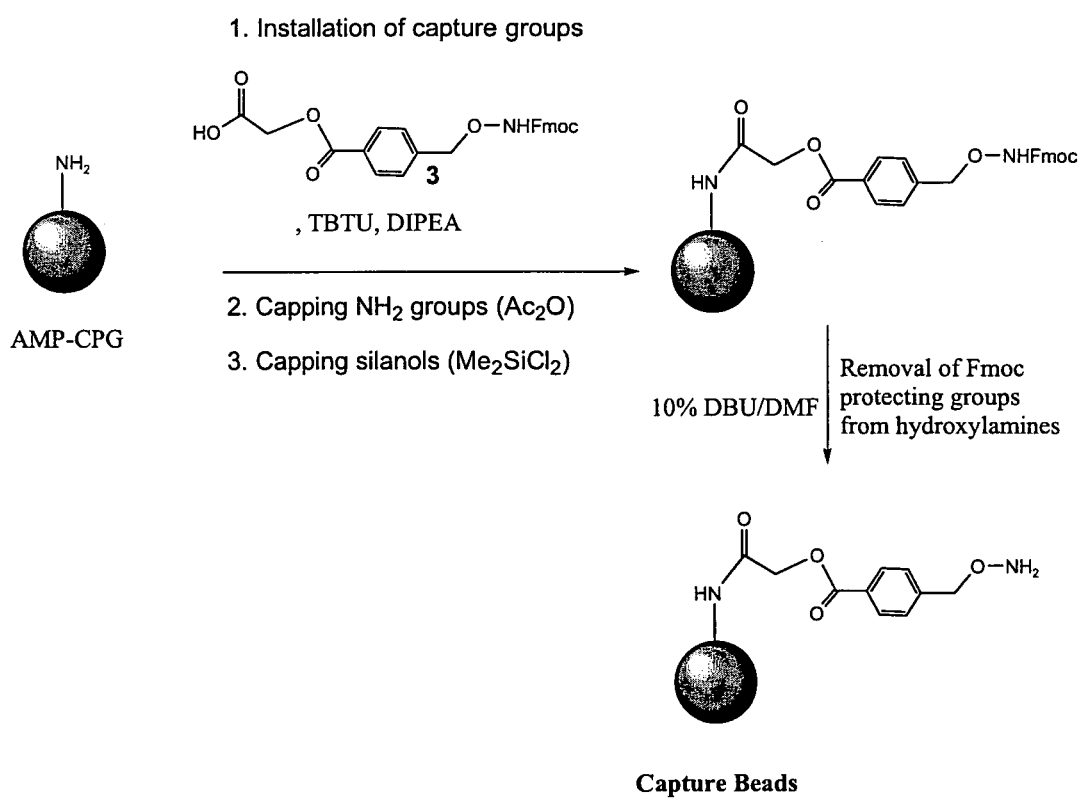

FIG. 10. Synthesis of Capture Beads

Figure 11:
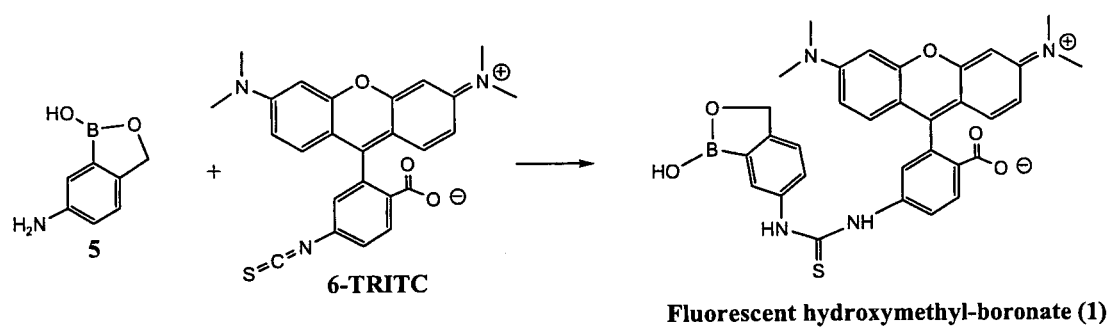

FIG. 11. Synthesis of fluorescent hydroxymethyl-boronate 1

Figure 12:
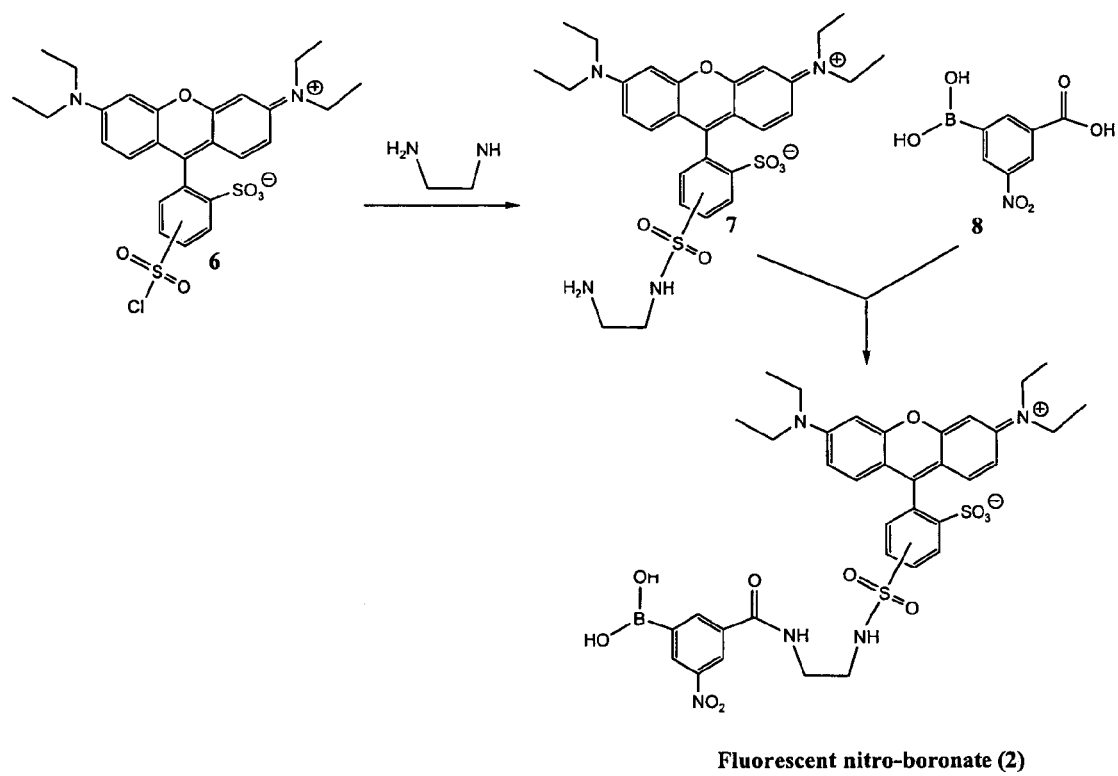

FIG. 12. Synthesis of fluorescent nitro-boronate 2

Figure 13:
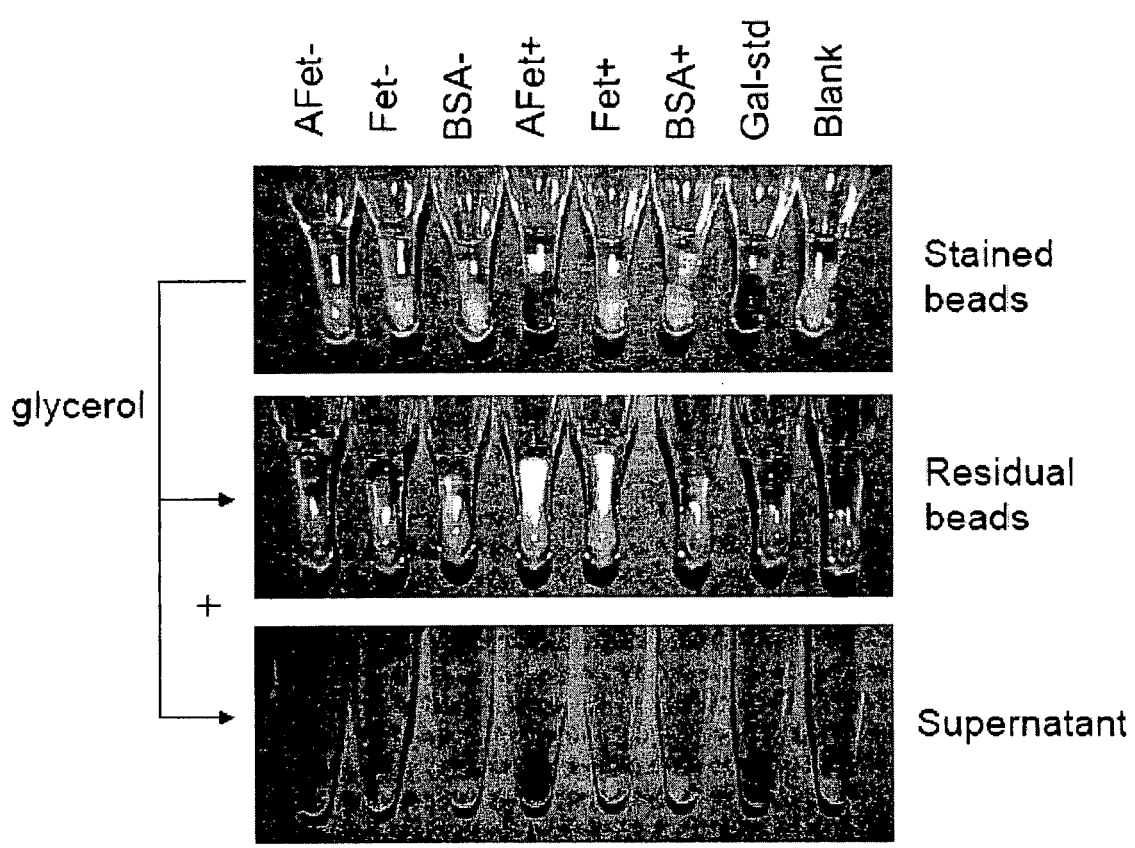

FIG. 13. Staining of treated capture beads with 1, and elution of 1 from stained beads with glycerol. Top panel: the beads designated AFet+ and Gal-std appear bright red, the others are white. Middle panel: after washing with glycerol all the beads appear white. Bottom panel: the glycerol washes of beads designated AFet+ and Gal-std appear bright red, the others are clear.

DETAILED DESCRIPTION OF THE INVENTION

Definitions

Aliphatic groups: Aliphatic compounds are non-aromatic organic compounds, in which carbon atoms are joined together in straight or branched chains rather than in rings. Aliphatics include not only the fatty acids and other derivatives of paraffin hydrocarbons (alkanes), but also unsaturated compounds, such as ethylene (the alkenes) and acetylene (the alkynes). The most frequently found non-carbon atoms bound to the carbon chain include hydrogen, oxygen, nitrogen, sulfur, and various halides.

Alicyclic compounds such as cycloalkanes are aliphatic compounds that have one or more non-aromatic cycles in their chemical structure. Bicycloalkanes have two rings of carbon joined at one or two carbons. Most aliphatic compounds have very exothermic combustion reactions, thus allowing hydrocarbons such as methane to fuel Bunsen burners in the laboratory, for example.

The aliphatic residue can be an optionally substituted linear aliphatic residue or an optionally substituted branched aliphatic residue. The aliphatic residue can also be an optionally substituted cyclic alkyl. "Cyclic alkyl" includes groups such as cyclopropyl, cyclobutyl, cyclopentyl, cyclohexyl, cycloheptyl, and cyclooctyl and such rings substituted with straight and branched chain alkyl groups as defined above. also includes polycyclic alkyl groups such as, but not limited to, adamantyl norbornyl, and bicyclo[2.2.2]octyl and such rings substituted with straight and branched chain alkyl groups as defined above. Thus, unsubstituted alkyl groups includes primary alkyl groups, secondary alkyl groups, and tertiary alkyl groups. Unsubstituted alkyl groups may be bonded to one or more carbon atom(s), oxygen atom(s), nitrogen atom(s), and/or sulfur atom(s) in a ligand. The cyclic aliphatic residue can e.g. comprise or consist of a C5-C16 cycloalkyl group. Shorter chain lengths can also occur, typically when the cycloalkyl is substituted with an aryl or heteroaryl residue. In one embodiment, the optionally substituted aliphatic residue comprises or consists of a C5-C20 alkyl group. Shorter chain lengths can also occur, typically when the alkyl is substituted with an aryl or heteroaryl residue. Further examples of alkyl groups substituted with aryl or heteroaryl includes, for example, a linear (C1-C10), branched (C4-C10) or cyclic (C5-C10) group, such as a methyl group, ethyl group, propyl group, such as a n-propyl group and an isopropyl group, butyl group, such as n-butyl group, isobutyl group, t-butyl group, n-amyl group, pentyl group, such as neopentyl group, cyclopentyl group, hexyl group, such as n-hexyl group, cyclohexyl group, heptyl group, octyl group, such as n-octyl group, nonyl group, such as n-nonyl group, decyl group, such as n-decyl group, undecyl group, dodecyl group, mentyl group, 2,3,4-trimethyl-3-pentyl group, 2,4-dimethyl-3-pentyl group, and the like.

Two preferred aliphatic groups are an ethyl or a methyl group.

Aromatic groups: The term "aromatic" or "aryl" moiety means either a mono- or polycyclic hydrocarbon group, which has a cyclic, delocalized (4n+2) pi-electron system, including arenes and their substitution products. Examples of suitable aromatic moieties for use in the present invention include, but are not restricted to, benzene, naphthalene, toluene, thiophene and pyridine.

Carbohydrate: The generic term 'carbohydrate' includes monosaccharides, oligosaccharides and polysaccharides as well as substances derived from monosaccharides by reduction of the carbonyl group (alditols), by oxidation of one or more terminal groups to carboxylic acids, or by replacement of one or more hydroxy group(s) by a hydrogen atom, an amino group, a thiol group or similar heteroatomic groups. It also includes derivatives of these compounds.

Glycose: "Glycose" in the present context refers to a monosaccharide, which can for example be either an aldose (a polyhydroxy aldehyde), a ketose (a polyhydroxy ketone), an oxidized derivative thereof including an alduronic acid (e.g. glucuronic acid), ketoaldonic acid (e.g. sialic acid or Kdo) as well as deoxy-derivatives and amino-derivatives thereof.

Sugar: The term "sugar" as used herein covers monosaccharides, oligosaccharides, polysaccharides, as well as compounds comprising monosaccharide, oligosaccharide, or polysaccharide. The terms "carbohydrate" and "sugar" are herein used interchangeably.

Oligo/poly-saccharide: Oligosaccharides and polysaccharides are compounds consisting of monosaccharides linked glycosidically. In general polysaccharides comprise at least 10 monosaccharide residues, whereas oligosaccharides in general comprise in the range of 2 to 20 monosaccharides. Oligosaccharides and polysaccharides may be linear or branched.

TAG: The term "TAG" in the present context, and in FIG. 1 (vide infra) is meant to indicate any atom, molecule or entity that can become covalently attached to another molecule thereby labelling said another molecule as having undergone the covalent attachment.

Monosaccharide: Parent monosaccharides are polyhydroxy aldehydes H—[CHOH]$_n$—CHO or polyhydroxy ketones H—[CHOH]$_n$—CO—[CHOH]$_m$—H with three or more carbon atoms. The generic term 'monosaccharide' (as opposed to oligosaccharide or polysaccharide) denotes a single unit, without glycosidic connection to other such units. It includes aldoses, dialdoses, aldoketoses, ketoses and diketoses, as well as deoxy sugars and amino sugars, and their derivatives, provided that the parent compound has a (potential) carbonyl group. Preferred examples of monosaccharides comprise in the range of 4 to 9 carbons, for example for polyhydroxy aldehydes n is an integer in the range of 3 to 8 and for polyhydroxyketones n+m is an integer in the range of 3 to 8. The term "Monosaccharide" can also include monosaccharide derivatives, such as those obtained by oxidation, deoxygenation, replacement of one or more hydroxyl groups by preferably a hydrogen atom, an amino group or thiol group, as well as alkylation, acylation, sulfation or phosphorylation of hydroxy groups or amino groups. Various categories of monosaccharides, all of which are envisaged as identifiable using the methods of the present invention, are described below:—

Monosaccharides with an aldehydic carbonyl or potential aldehydic carbonyl group are called aldoses; those with a ketonic carbonyl or potential ketonic carbonyl group, ketoses. The term 'potential aldehydic carbonyl group' refers to the hemiacetal group arising from ring closure. Likewise, the term 'potential ketonic carbonyl group' refers to the hemiketal structure.

Cyclic hemiacetals or hemiketals of sugars with a five-membered (tetrahydrofuran) ring are called furanoses, those with a six-membered (tetrahydropyran) ring pyranoses.

Monosaccharides containing two (potential) aldehydic carbonyl groups are called dialdoses)

Monosaccharides containing two (potential) ketonic carbonyl groups are termed diketoses Monosaccharides containing a (potential) aldehydic group and a (potential) ketonic group are called ketoaldoses.

Monosaccharides in which an alcoholic hydroxy group has been replaced by a hydrogen atom are called deoxy sugars Monosaccharides in which an alcoholic hydroxy group has been replaced by an amino group are called amino sugars. When the hemiacetal hydroxy group is replaced, the compounds are called glycosylamines.

The polyhydric alcohols arising formally from the replacement of a carbonyl group in a monosaccharide with a CHOH group are termed alditols.

Monocarboxylic acids formally derived from aldoses by replacement of the aldehydic group by a carboxy group are termed aldonic acids.

Oxo carboxylic acids formally derived from aldonic acids by replacement of a secondary CHOH group by a carbonyl group are called ketoaldonic acids.

Monocarboxylic acids formally derived from aldoses by replacement of the CH2OH group with a carboxy group are termed uronic acids.

The dicarboxylic acids formed from aldoses by replacement of both terminal groups (CHO and CH2OH) by carboxy groups are called aldaric acids.

Glycosides: Glycosides are mixed acetals formally arising by elimination of water between the hemiacetal or hemiketal hydroxy group of a sugar and a hydroxy group of a second compound. The bond between the two components is called a glycosidic bond.

Method for Analysis of a Terminal Monosaccharide on a Glycosylated Substrate

In a first aspect of the present invention is provided a method for analysis of a terminal monosaccharide on a glycosylated substrate, said method comprising the steps of:—
(i) detaching said monosaccharide from said glycosylated substrate, preferably using an exoglycosidase;
(ii) allowing said detached monosaccharide to covalently bind to a capture group on a solid support;
(iii) incubating said covalently bound monosaccharide with a detection agent with formula X:
TAG-R-Boronate
wherein TAG=a tag moiety capable of being detected
R=organic moiety
Boronate=a boronic acid moiety or ester thereof,
said boronate being attached to a carbon atom comprised in said R group;
(iv) allowing the detection agent to bind the monosaccharide
(v) detecting detection agent having bound to the monosaccharide.

In one embodiment of the invention it is preferred that the above method does not comprise a step of reducing the bond between the capture group and the monosaccharide after immobilisation to the solid support. Thus, for example it is preferred that if the monosacchride is bond to the solid support via a C═N linkage, then said C═N is not intentionally reduced by contacting the immobilised monosaccharide with a reducing agent such as with a borane or a borohydride.

In another embodiment it is preferred that the immobilised monosaccharide is not contacted with a reducing agent before or simultaneously with incubation with the detection agent.

The stages of the method are described in more detail herein below:—

(i) Detaching Said Monosaccharide From Said Glycosylated Substrate

Figure 1:
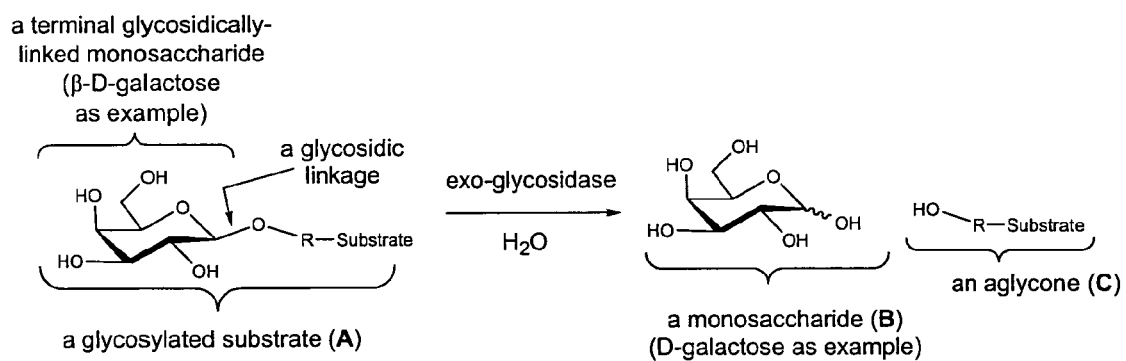
FIG. 1. Release of a terminal monosaccharide from a glycosylated substrate using an exo-glycosidase. In the present example, the exo-glycosidase is a β-galactosidase that cleaves the terminal β-galactose residue to release the free monosaccharide (D-galactose) from a substrate leaving the degalactosylated aglycone.

Stage (i) of the method of the present invention comprises the step of detaching a monosaccharide from a glycosylated substrate A (see e.g. FIG. 1)

In one embodiment of the invention it is preferred that said glycosylated substrate is not an immobilised sugar of the general structure Sugar-C=N-linker-Spacer-Solid.

Monosaccharide: In a preferred embodiment, the monosaccharide is a naturally occurring monosaccharide or a monosaccharide which has been liberated from a naturally occurring or recombinantly produced compound comprising a carbohydrate, preferably without having been subject to furthermore modifications after liberation.

In one preferred embodiment of the present invention, the monosaccharide is a glycose, such as selected from the group consisting of: an aldose, a ketose, a deoxy sugar, an amino sugar, and derivatives thereof, such as an oxidized derivative thereof.

Examples of suitable glycoses include galactose, fucose, N-acetylglucosamine, galacturonic acid, and sialic acid.

Any glycosylated substrate comprising monosaccharides that is known to one skilled in the art can be used in the methods of the present invention. For example, said glycosylated substrate can be selected from the group consisting of: a glycosylated antibiotic, a glycoprotein, a glycolipid, a glycosylated steroid, an oligosaccharide, a polysaccharide.

In one preferred embodiment of the present invention, the glycosylated substrate is a substrate obtainable from a eukaryotic organism. Thus, the glycosylated substrate can be selected from the group consisting of: a glycoprotein, a glycolipid or a proteoglycan; preferably derived from a eukaryotic organism. In another embodiment, said glycosylated substrate is selected from the group consisting of: a glycoprotein, a glycolipid or a proteoglycan, preferably obtainable or obtained from the cell membrane of a eukaryotic cell.

It can also be desirable to carry out the method of the present invention on a glycosylated substrate obtainable from a prokaryotic organism. Thus, in one embodiment of the present invention, the glycosylated substrate is selected from the group consisting of: a glycoprotein, a glycolipid, a lipopolysaccharide, or a polysaccharide, obtainable or obtained from a prokaryotic organism. In another embodiment, the glycosylated substrate is selected from the group consisting of: a glycoprotein, a glycolipid, a lipo-polysaccharide, or a polysaccharide obtainable from or obtained from the cell surface or membrane of a prokaryotic organism.

In another embodiment, the glycosylated substrate is selected from the group consisting of: a glycosylated antibiotic, a glycosylated steroid, a glycosylated natural product or a glycosylated peptide.

Glycosylated substrates may be derived from a variety of sources. For example the glycosylated substrate may be obtained from a living organism or part of a living organism, such as animals or plants or from one or more specific animal or plant tissues, from organisms such as prokaryotic or eukaryotic cells, from viruses, from in vitro cultivated mammalian cells, insect cells, plant cells, fungi, bacterial cells, yeast, or phages. For example the glycosylated substrate may be isolated from extracts of any of the aforementioned cells, microbial organisms or living organisms. Such extracts may comprise glycosylated substrates, such as free carbohydrates. Extracts may also comprise compounds comprising monosaccharide, oligosaccharide, polysaccharide or carbohydrate moieties, notably glycoproteins or glycolipids or small organic molecules to which carbohydrates are attached, which are generally referred to as glycosides. Glycoproteins are compounds in which a carbohydrate component is linked to a peptide, polypeptide or protein component. Thus as used herein the term glycoprotein also cover proteoglycans and glycosaminoglycans. Glycolipids are compounds containing one or more monosaccharide, oligosaccharide, polysaccharide or carbohydrate moieties bound by a glycosidic linkage to a hydrophobic moiety such as an acylglycerol, a sphingoid, a ceramide (N-acylsphingoid) or a prenyl phosphate. Glycosides can for example be small (MWt 100-5000) organic molecules glycosidically linked to one or more sugars via either O, N or S.

Glycosylated substrates may also be the products of chemical synthesis, or chemical/enzymatic synthesis, such as oligosaccharides prepared in vitro by chemical synthesis in solution or on the solid phase. These same synthetic oligosaccharides may be further modified by enzymatic reaction, such as for example by the sulfation, phosphorylation or glycosylation. Thus the methods described herein may also be used for identification of monosaccharides of synthetic or semi-synthetic oligosaccharides or oligosaccharide libraries.

Optionally, the glycosylated substrate to be analysed can be comprised within a sample—for example, a complex sample, such as a sample comprising non-glycosylated substrates. It can thus be beneficial in some embodiments that the method of the present invention comprises an additional step after step (i), wherein (preferably high molecular weight) components of said sample are removed, such as for removal of macromolecules, such as larger polysaccharides or non-polysacharide components, particularly polypeptides. One method of removing said components is by size exclusion, preferably by ultrafiltration or by dialysis. Another method of removing the said components involved passing the sample through a membrane that is permeable to the monosaccharide but not to molecules with high molecular weights, such as proteins. Said membrane can for example be a Centricon (Millipore) membrane or a dialysis membrane. In another embodiment, said components of the sample are removed by absorption on hydrophobic phases such as C18 or carbon.

Detachment step:—The detachment step of step (i) can be carried out by a range of methods known to one skilled in the art. Preferably, said detachment step is carried out using an exo-glycosidase, such as a bacterial exo-glycosidase, such as for example an exo-glycosidase selected from the group consisting of:

alpha-mannosidase, alpha-glucosidase, alpha-galactosidase, alpha-xylosidase, alpha-fucosidase, alpha-N-acetylglucosaminidase, alpha-N-acetylgalactosaminidase, alpha-glucuronidase, alpha-iduronidase, alpha-sialidase, beta-mannosidase, beta-glucosidase, beta-galactosidase, beta-xylosidase, beta-fucosidase, beta-N-acetylglucosaminidase, beta-N-acetylgalactosaminidase, beta-glucuronidase, beta-iduronidase and beta-sialidase.

Thus, said terminal monosaccharide can be detached using glycosidases acting on bacterial polysaccharides or glycolipids, cleaving deoxy sugars, amino sugars, substituted amino sugars, branched chain sugars, O-methyl sugars and the like.

Many useful glycosidases are further described in the art, for example any of the glycosidases described in U.S. Pat. No. 5,100,778 or WO 92/19974 may be employed with the present invention.

An example of the release of a terminal monosaccharide from a glycosylated substrate using an exo-glycosidase is shown in FIG. 1:—

The soluble substrate monosaccharide-O—R-Substrate (A) is incubated with an exo-glycosidase of known specificity in a solution in which the glycosidase is soluble, typically a buffer solution with or without added cations. The exo-glycosidase is capable of cleaving a single terminal monosaccharide residue from a glycoside. The R group in A is preferably a carbohydrate (such as a monosaccharide or oligosaccharide) unit or an amino acid in glycoproteins or glycopeptides, a glycose unit in polysaccharides or oligosaccharides, a glycose unit or a lipid in glycolipids, or a glycose unit or an organic aglycone in e.g. glycosylated antibiotics or steroids. If the terminal monosaccharide unit has a structure and anomeric configuration (either α or β) that is hydrolysable by the glycosidase, it is cleaved to produce a reducing sugar (monosaccharide, B) and the aglycone (HO—R-substrate, C).

The specificities of many glycosidases are known, and such well-characterized glycosidases have been used in the sequencing of oligosaccharides. Thus, these enzymes can be specific for the stereochemistry of the monosaccharide-rings and the α or β configuration of the glycosidic linkages. Many of them are also specific with respect to the exact position of attachment of the glycose to the next sugar. For example, some α-glycosidases cleave only α1-3 linkages and others only α1-6 linkages. Thus, the entire structure of an oligosaccharide can sometimes be determined by successive glycosidase digestion.

In another embodiment, the terminal monosaccharide is detached chemically, such as for example using acid hydrolysis, such as mild acid hydrolysis. For mild hydrolysis one can, for example, treat the glycosylated substrate with 0.1 N aq. trifluoroacetic acid at 80 degrees Celsius for 1 h. O-linked monosaccharides may be cleaved from glycoproteins by chemical methods, such as alkaline β-elimination or enzymatically using enzymes such as an O-glycosidase. Monosaccharides may also be cleaved from small organic molecules using either acidic or basic reactions.

(ii) Allowing Said Detached Monosaccharide to Covalently Bind to a Capture Group on a Solid Support Stage (ii) of the method of the present invention comprises the step of allowing said detached monosaccharide to covalently bind to a capture group on a solid support.

Figure 2:
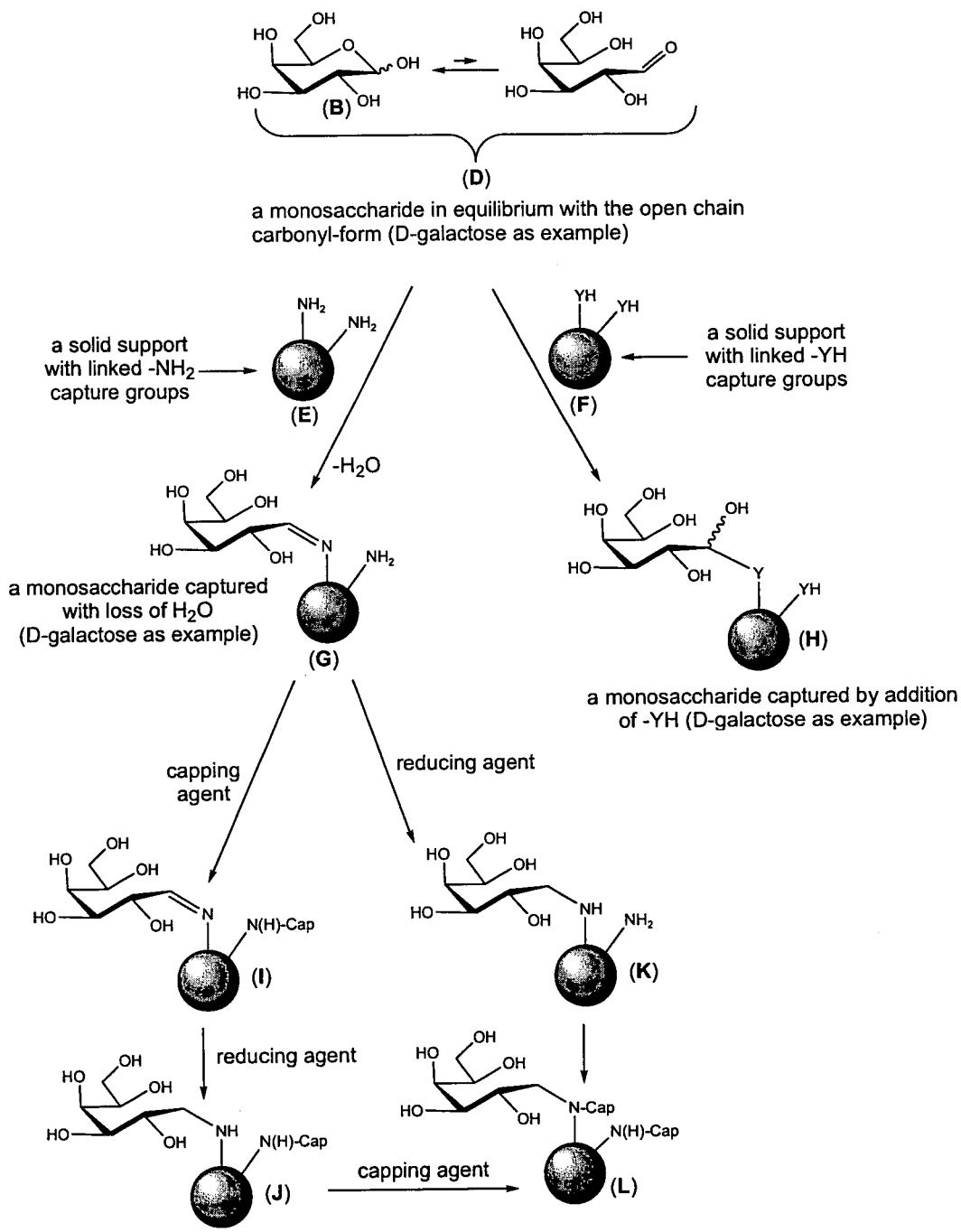
FIG. 2. Capture of and further optional processing of a monosaccharide on solid supports using two types of capture groups. The equilibrium between the closed-ring form and the open-chain carbonyl of the released monsoaccharide B is shown in D. The carbonyl form reacts with immobilized —NH$_2$ groups on E, with loss of water, to give G. Unreacted —NH$_2$ groups in G can be capped to yield I, the C=N bond in I can be reduced to give J wherein the —NH group can also be capped to give L. The initial capture product G can also be reduced directly to K, which can be further capped to give L. A second type of solid-support F bearing —YH capture groups can also react directly with the open-chain carbonyl group in D, by addition to give H.

Capture group:—By "capture" group is meant a reactive chemical group capable of making a covalent bond by nucleophilic attack at the carbonyl group of the liberated monosaccharide (B). Examples of two different versions of this "capture" step are illustrated in FIG. 2:—The equilibrium between the closed-ring form and the open-chain carbonyl of the released monosaccharide B is shown in D. The carbonyl form reacts with immobilized (e.g. $NH_2$)-capture groups linked to the solid support (E), to give a captured monosaccharide (G). Unreacted capture groups in G can optionally be capped to yield "capped" capture groups (I), optionally with further reducing and/or capping steps, to give J and L. The initial capture product G can also be reduced directly to K, which can be further capped to give L. In an alternative embodiment, a second type of solid-support F bearing —YH capture groups can also react directly with the open-chain carbonyl group form of the monosaccharide in D, by addition to give a monosaccharide captured as H. Preferably, the covalent adduct formed between the monosaccharide bound to the capture group on the solid support comprises at least two —OH— groups.

Many suitable capture groups for use in the method of the present invention are known by one skilled in the art. Preferably, the capture group comprises or consists of an —NHR group, where R is selected from the group consisting of: an alkyl, aryl, substituted alkyl or substituted aryl group. For example, the capture can comprise or consist of an —$NH_2$ group. In one preferred embodiment, the capture group comprises or consists of the structure -M-$NH_2$, wherein M is a heteroatom.

In one embodiment, the capture group comprises or consists of a sulphur atom or phosphorous atom.

In another preferred embodiment, the capture group comprises or consists of an acidic —CH— group capable of ionization to a carbanion an subsequent nucleophlic attack at the sugar aldehyde. Compounds of this type are known by one skilled in the art and typically include a CH group adjacent to one or more of the follow groups:— one or more carbonyl groups (—CH—CO—),
a nitrile group (giving e.g. —CH—CN)
a nitro group (giving e.g. —CH—NO2)
a sulfone group (giving e.g. —CH—SO2—)
Capture groups comprising at least one —$NH_2$ group:
According to one preferred embodiment of the present invention the linker comprises a capture group, wherein the capture group comprises at least one —$NH_2$ group. In a favourable format, the capture group terminates in an —$NH_2$ group that is attached to the linker through an optional group R. Thus the capture group preferably is of the structure R—$NH_2$. R may be a simple alkyl, aryl or substituted alkyl or aryl group. Preferably, R should contain a heteroatom directly attached to the —$NH_2$ group, to produce structures of the type linker-M-$NH_2$, wherein M is a heteroatom (i.e. not carbon), preferably M is selected from the group consisting of N, O and S. Especially favourable are compounds where M is a heteroatom, such as in the structures linker-O—$NH_2$, linker-NH—$NH_2$, linker-CO—NH—$NH_2$, linker-NH—CO—NH—$NH_2$, linker-S(O)$_2$NH—$NH_2$ and linker-S—$NH_2$.

In this embodiment, the capture of the monosaccharide is done by reacting the —$NH_2$ group of the capture group with e.g. the reducing end of said monosaccharide, i.e. with the aldehyde, ketone or hemiacetal group. The reaction can occur at any pH values but is most favored in the range of pH 2-9. The methods may involve the addition of one or more additives, such as additives which may either facilitate or favourably alter the equilibrium between the open chain aldehyde form of the monosaccharide and the hemiacetal form of the monosaccharide, wherein the open chain aldehyde form is preferred. The additive may for example be metal ions, boronates or silicates. The capture produces a species attached to the solid support through a covalent double bond (shown as C=N) where the C is derived from the monosaccharide moiety and N from the capture group. This immobilized monosaccharide may also be in equilibrium with its cyclic ring form, in particular if the monosaccharide was a pyranose, then the immobilised monosaccharide may be in equilibrium with its cyclic 6-membered ring form (see for example compounds B and D of FIG. 2), but it may also be in equilibrium with its 5-membered ring form if the appropriate OH group on the monosaccharide is unsubstituted.

Linker group: The capture group can optionally be attached to the solid support via a linker group. Said linker group can be any molecule capable of linking the capture group to the solid support. The linker may be any of a large variety of linkers such as those in common use in solid-phase organic synthesis. The linker may either be a non-cleavable linker or a cleavable linker.

Non-cleavable linkers may for example be alkyl, aryl, ethers or amides, wherein any of the aforementioned may optionally be substituted. For example any of the aforementioned may be substituted with heteroatoms or they may contain, O-alkyl,alkyl, aryl or heteroatoms as branches. In one example the linker comprises or essentially consists of PEG and/or polyamide.

The linker may comprise a site where a reaction can be made to occur to sever the part containing the capture group (including the molecules it has captured and which have been optionally further modified) from the solid support. Such linkers are referred to as cleavable linkers, and are in wide use in solid phase organic synthesis. Examples of cleavable linkers are known where the cleavage can be effected by electrophiles, nucleophiles, oxidizing agents, reducing agents, free radicals, acid, base, light, heat or enzymes.

Cleavable linkers may for example be acid labile (for example, the Rink amide as described in Rink, 1987, *Tetrahedrom Lett.*, 28: 387 and traceless silyl linkers as described in Plunkett et al., 1995, *J. Org. Chem.*, 60: 6006-7), base labile (for example, HMBA as described in Atherton et al. 1981, *J. Chem. Soc. Perkin Trans,* 1: 538), or photolabile (for example, 2-nitrobenzyl type as described in Homles et al., 1995, *J. Org. Chem.*, 60: 2318-2319). The linkers may be more specific and restrictive of the type of chemistry performed, such as silyl linkers (for example, those cleaved with fluoride as described in Boehm et al., 1996, *J. Org. Chem.*, 62: 6498-99), allyl linkers (for example, Kunz et al., 1988, *Angew. Chem. int. Ed. Engl.*, 27: 711-713), and the safety catch sulfonamide linker (for example, as described in Kenner et al., 1971, *Chem. Commun.*, 12: 636-7). Enzyme cleavable linkers may for example be any of the enzyme cleavable linkers described in Reents et al., 2002, Drug Discov. Today, 7: 71-76, or any functionalised derivatives of the enzyme-labile protecting groups described in the review by Waldmann et al., 2001, Chem. Rev. 101: 3367-3396. Heat labile linkers may for example be of the type described in Meng et al., 2004, Angew. Chem. Int. Ed., 43: 1255-1260.

Reaction conditions: The capture reaction may be performed in any useful solvent. A person of ordinary skill in the art will readily be able to identify a useful solvent for any given compound. The solvent may for example be selected from the group consisting of water, aqueous buffer, organic solvents and mixed aqueous and organic solvents. The solvent may also be any of the aforementioned comprising one or more additives such as acids, bases, organic amines, anilines, salts, divalent metal cations, detergents, complexing agents including inclusion-complex-forming molecules such as cyclodextrins or calixarenes, chelating agents (for example EDTA), borates, boronates or silicates.

In a preferred embodiment the amount of solid support added to the reaction is adjusted so that a molar excess of capture groups are present in relation to the monosaccharide, preferably said excess is large, such as at least 2 times, preferably at least 5 times, more preferably at least 10 times, such as at least 50 times, for example at least 100 times or more. This excess will ensure a more efficient capture of the monosaccharide.

The capture reaction may be carried out at any temperature, but preferably at temperatures in the range of 0 to 100° C.

Solid support: Any suitable solid support capable of supporting the capture groups and known to one skilled in the art can be used in the methods of the present invention. For example, the solid support can be selected from the group consisting of polymers, solids, insoluble particles and surfaces. Examples include PEGA and SPOCC.

The solid support is preferably a bead. In another preferred embodiment, the solid support is a slide, such as a glass slide, a microtiter well, or a metal-coated slide, for example a gold-coated slide. The solid support can be a hydroxylamine-modified surface, in which case it is preferably a controlled pore glass (CPG) bead or glass slide.

The term "solid support" as used herein covers physical solids as well as insoluble polymers, insoluble particles, surfaces, membranes and resins, preferably the solid support is an insoluble polymer, an insoluble particle, a surface or a resin.

Thus the "solid support" may be an insoluble inorganic matrix (such as glass), an insoluble polymer (such as a plastic, for example polystyrene), an insoluble matrix consisting of parts of both organic and inorganic components (e.g. some hybrid silicates, such as compounds of the structure R—Si—O—), organic polymers in common use in solid-phase synthesis (polystyrenes, PEGA resins, PEG resins, SPOCC resins and hybrids thereof), polyethylene glycol chains (which can be soluble in certain organic solvents and made insoluble by the addition of other solvents). The solid may also be a metal (such as gold), an alloy, or a composite such as for example indium-tin oxide or mica.

Organic polymers used in solid-phase synthesis for example include: TentaGel (commercially available from Rapp polymere, Tübingen, Germany), ArgoGel (commercially available from Argonaut Technologies Inc., San Carlos, Calif.), PEGA (commercially available from Polymer Laboratories, Amherst, Mass.), POEPOP (Renil et al., 1996, *Tetrahedron Lett.*, 37: 6185-88; available from Versamatrix, Copenhagen, Denmark) and SPOCC (Rademann et al, 1999, *J. Am. Chem. Soc.*, 121: 5459-66; available from Versamatrix, Copenhagen, Denmark).

In one embodiment of the invention the solid support is a sensor, such as a surface acoustic wave sensor (such as any of the sensors described in Samoyolov et al. 2002, J. Molec. Recognit. 15: 197-203), a surface plasmon resonance sensor (such as any of the sensors reviewed by Homola et al., 1999, Sensors and Actuators B, 54: 3-15), or a nanomechanical cantilever sensor such as described by Mukhopadhyay in Nano Lett. 2005, 5, 2385-88.

Such solid supports may be inorganic materials such as glass, metals such as gold, organic polymeric materials or hybrids thereof and may be covered various coatings such as proteins or polysaccharides, oligomers such as dendrimers or polymers such as polyacrylamide or polyethylene glycol.

In a preferred embodiment the solid support is glass.

Washing: Once the terminal monosaccharide has been immobilised on the solid support through reaction with the capture group (see e.g. steps exemplified in FIG. 2), the solid supports can optionally be washed to remove non-covalently bound material. Accordingly, if the glycosylated substrate is, for example, provided in a sample comprising other compounds, the reducing sugar may be purified from said sample. It is thus comprised within the present invention that the glycoslated substrate is provided in a non-purified form.

The skilled person will readily be able to identify suitable washing conditions for a given immoblised monosaccharide (e.g. any of compounds G-L in FIG. 2). The washing may for example be done with any of the herein-mentioned solvents optionally comprising any of the herein-mentioned additives in addition to detergents and denaturing agents. The washing may be performed at any temperature, but preferably at temperatures in the range of 0-100° C.

(iii) Incubating Said Covalently Bound Monosaccharide With a Detection Agent

Stage (iii) of the method of the present invention comprises the step of incubating said covalently bound monosaccharide with a detection agent with formula X:

TAG-R-Boronate wherein TAG=a tag moiety capable of being detected

R=organic moiety

Boronate=a boronic acid moiety or ester thereof, said boronate being attached to a carbon atom comprised in said R group. Preferably, an excess of said detection agent is used.

By "Boronate" is meant any suitable chemical moiety comprising a boronic acid moiety, or an ester thereof, preferably the boronate is boronic acid.

The detection agent can for example comprise aryl boronate or heteroarylboronate. The process is shown schematically in FIG. 3.

It is preferred that the detection agent has a formula selected from the group consisting of:—

TAG-R—B(OH)$_2$, TAG-R—B(OH)(OR') or TAG-R—B(OR')(OR")

wherein R' and R" may be either aliphatic or aromatic and are optionally covalently attached to R, for example resulting in a cyclic boronate structure. For example R' and R" may individually be selected from the group consisting of $C_{1-6}$ linear or branched alkyl, $C_{5-7}$ aliphatic ring and $C_{5-7}$ aromatic ring. In the event R is a ring, R' may also form a fused ring with R, and in this embodiment R' may be a 4-7 membered aliphatic heterocycle, which is optionally substituted. For example, said heterocycle may be a 5 membered cycle including the B and the O atom to which R' is attached. Said heterocycle may not be substituted or it may be substituted.

Figure 5:
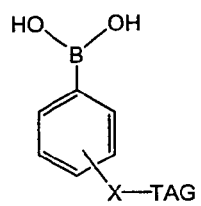
FIG. 5. Examples of structures a-c of TAG-R-Boronate M.
 a) Phenyl boronic acid derivatives:
  X=alkyl, aryl, heteroaryl, substituted alkyl, substituted aryl, substituted heteroaryl, fused alkyl or heteroaryl ring, NH, O, S, CO,
  X-TAG substituent may be o, m or p to the boron
  Example: X=m-NH, TAG=Tetramethylrhodamine;
 b) Phenyl boronic acid derivatives with an o-aminometyl moiety:
  X=alkyl, aryl, heteroaryl, substituted alkyl, substituted aryl, substituted heteroaryl, fused alkyl or heteroaryl ring, NH, O, S, CO,
  X-TAG substituent may be o, m or p to the boron
  R=H, alkyl, cycloalkyl, aryl, substituted alkyl, substituted cycloalkyl, substituted aryl. Example: X=p-NH, TAG=Tetramethylrhodamine, R=Me;
 c) Phenyl boronic acid derivatives with a substituted o-aminomethyl moiety:
  X=alkyl, aryl, heteroaryl, substituted alkyl, substituted aryl, substituted heteroaryl, fused alkyl or heteroaryl ring, NH, R=H, alkyl, cycloalkyl, aryl, substituted alkyl, substituted cycloalkyl, substituted aryl.
  Example: X=CH$_2$, TAG=Tetramethylrhodamine, R=H
The free acid form of the boronate is shown, though esters are also implied.
Figure 5:
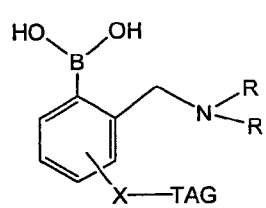
Figure 5:
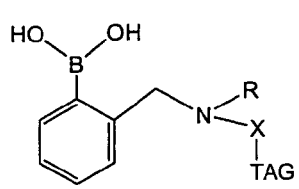

Thus, in one embodiment of the present invention, the TAG-R-Boronate comprises a Phenyl boronic acid derivative, such as as exemplified by group a) in FIG. 5.

In another embodiment of the present invention, the TAG-R-Boronate comprises a Phenyl boronic acid derivative with an o-aminomethyl moiety such as as exemplified by group b) in FIG. 5.

In another embodiment of the present invention, the TAG-R-Boronate comprises a Phenyl boronic acid derivative with a substituted o-aminomethyl moiety, such as as exemplified by group c) in FIG. 5.

Figure 6:
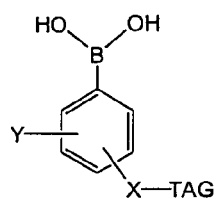
FIG. 6. Examples d-f of structures of TAG-R-Boronate M.
 d) Phenyl boronic acid derivatives bearing an electronegative substituent:
  X=alkyl, aryl, heteroaryl, substituted alkyl, substituted aryl, substituted heteroaryl, fused alkyl or heteroaryl ring, NH, O, S, CO,
  X-TAG and Y substituents may be o, m or p to the boron
  Y=electronegative group such as NO$_2$, COOR, CN, COR, SO$_2$OH, SO$_2$R, CF$_3$(R=H, alkyl or aryl)
  Example: Y=m-NO$_2$, X=m-CONHCH$_2$CH$_2$NH—, TAG=Lissamine (2);
 e) Pyridine boronic acid derivatives:
  X=alkyl, aryl, heteroaryl, substituted alkyl, substituted aryl, substituted heteroaryl, fused alkyl or heteroaryl ring, NH, O, S, CO, B and X-TAG substituent may be o, m or p to ring Nitrogen
Example: X=m-NH, m-B(OH)$_2$, TAG=Tetramethylrhodamine.
Figure 6:
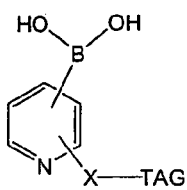
Figure 6:
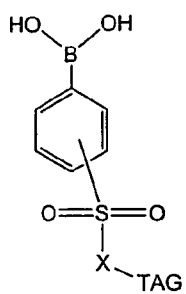

In another embodiment of the present invention, the TAG-R-Boronate comprises a Phenyl boronic acid derivative bearing an electronegative substituent, such as as exemplified by group d) in FIG. 6.

In another embodiment of the present invention, the TAG-R-Boronate comprises a Phenyl boronic acid derivative with a sulfonamide or a sulfone substituent, such as as exemplified by group e) in FIG. 6.

In another embodiment of the present invention, the TAG-R-Boronate comprises a pyridine boronic acid derivative, such as as exemplified by group f) in FIG. 6.

In another embodiment of the present invention, the TAG-R-Boronate comprises a Phenyl boronic acid derivative bearing an o-hydroxymethyl group, such as as exemplified by group g) in FIG. 7.

In another embodiment of the present invention, the TAG-R-Boronate comprises a Phenyl boronic acid derivative bearing a substituted o-hydroxymethyl group, such as as exemplified by group h) in FIG. 7.

In another embodiment of the present invention, the TAG-R-Boronate comprises a Phenyl boronic acid derivative bearing a quaternary ammonium substituent, such as as exemplified by group i) in FIG. 7.

In another embodiment of the present invention, the TAG-R-Boronate comprises a Multiple aryl boronic acid derivative, such as as exemplified by group j) in FIG. 8.

In another embodiment of the present invention, the TAG-R-Boronate comprises a Boronic acid derivative of an aromatic 5-membered ring heterocycle, such as as exemplified by group k) in FIG. 8.

In another embodiment of the present invention, the TAG-R-Boronate comprises a Phenyl boronic acid derivative with 2 or more fused rings, such as 2, 3, 4, 5 or 6 rings, such as as exemplified by group I) in FIG. 8.

In one preferred embodiment, the detection agent has the formula of the tetramethylrhodamine-derived fluorescent hydroxymethyl-boronate 1 shown in FIG. 11.

In another preferred embodiment, the detection agent is according to the formula of the lissamine-derived fluorescent nitro-boronate 2 shown in FIG. 12.

The R moiety can be any chemical group, such as an aliphatic or aromatic moiety, as described herein. Thus, R may for example be an aromatic cycle or heteroaromatic cycle, such as a 5 to 6 membered aromatic or heteroaromatic cycle or a fused ring aromatic ring system, for example 2 fused rings of each 5 to 6 members fused at any two positions (see e.g. FIG. 8, I). For example, the heteroaromatic cycle may be a 5 to 6 membered ring, such as a 5 membered ring comprising in the range of 1 to 3, such as 1, for example 2 heteroatoms selected from the group consisting of N, O and S. Said aromatic cycle or heteroaromatic cycle may optionally be substituted, for example substituted with alkyl, such as $C_{1-6}$ alkyl, amino alkyl, such as $C_{1-6}$ amino alkyl, for example $C$—$NR^x_2$, a primary or secondary or tertiary amino group or sulphate, wherein $R^x$ may be —H, alkyl, cycloalkyl, aryl, substistuted alkyl, substitued cycloalkyl or substituted aryl, such as —H, $C_{1-6}$ alkyl, $C_{5-7}$ cycloaryl or $C_{5-7}$ aryl.

In a preferred embodiment said aromatic or heteroaromatic cycle is substituted with X-TAG, or one of aforementioned substiuents are covalently attached to X-TAG, wherein X is selected from the group consisting of —NH—, —CO—, alkyl (such as C1-6 alkyl, for example methyl or ethyl), aryl (such as C5 to 7 aryl), heteroaryl (such as a 5 to 7 membered aryl cycle), substituted alkyl, substituted aryl, substituted heteroaryl, fused alkyl or heteroalkyl, heteroaryl ring, —O— and —S—. For example, X may be selected from the group consisting of —NH—, —CO—, —CH$_2$—, —CH$_2$—CH$_2$—, phenyl, —O— and —S—.

Figure 4:
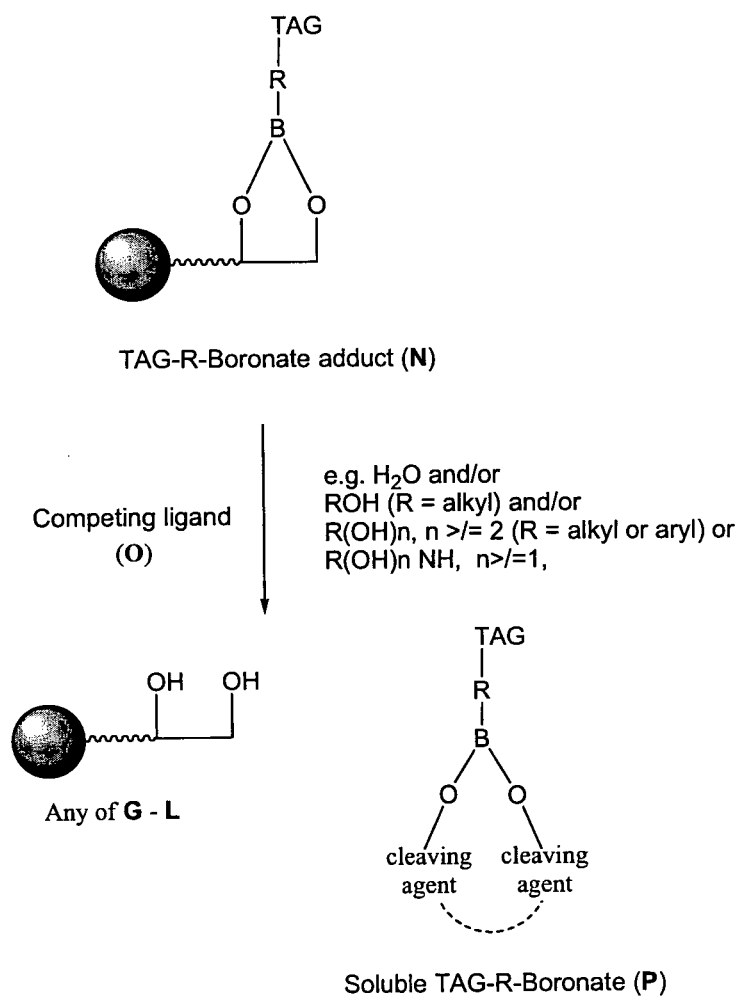
FIG. 4. Release of bound TAG-R-Boronate (P) back into solution from the insoluble complex N using a competing ligand O. The structure of P will depend on the structure of the competing ligand, but will incorporate OH, OR or N groups bound to the boron atom.

It may be desirable to release the detection agent from the solid support either before or after the detection step, for example to improve quantification of certain types of detection agent. However, in some embodiments of the invention the detection agent is not released from the solid support. The release step may for example be effected by contacting the solid support with a solution of a soluble compound that competes with the detection agent for binding of the monosaccharide, as shown in FIG. 4.

Said soluble compound can, for example, be a polyalcohol such as glycerol or glucitol, or an amino-alcohol such as diethanolamine.

TAG moiety:—The detection agent is preferably provided comprising a TAG moiety. Any suitable TAG moiety can be used, such as e.g. selected from the group consisting of: a fluorescent moiety, a luminescent moiety, and a coloured moiety. Suitable specific moieties include, inter alia, coumarin, tetramethylrhodamine, lissamine or fluorescein.

In one preferred embodiment of the invention the TAG has beneficial spectroscopic properties. By beneficial spectroscopic properties is meant that the TAG can easily be visualised, for example by spectrometry. Thus the TAG may for example be spectroscopically detectable. In a preferred embodiment the TAG is a fluorescent TAG. Examples of such TAGs can be found in the Handbook of Fluorescent Probes and Research Products, by RP Haugland, 9$^{th}$ Ed., Molecular Probes.

The product of addition of such a TAG can absorb and re-emit light that can be detected. The number of such TAGs present on the solid support will reflect the number of monosaccharides captured on the solid support. The number of monosaccharides originally present in a sample can therefore be estimated by the fluorescence of the TAG, provided that the provided solid supports comprise an excess of capture groups. TAGs other than fluorescent molecules can also be used. These can include radioactive TAGs, phosphorescent TAGs, chemiluminescent TAGs, UV-absorbing TAGs, nanoparticles, quantum dots, coloured compounds, electrochemically-active TAGs, infrared-active TAGs, TAGs active in Raman spectroscopy or Raman scattering, TAGs detectable by atomic force microscopy or TAGs comprising metal atoms or clusters thereof.

If the solid support is a sensor, such as a surface acoustic wave sensor, a surface plasmon resonance sensor, or a cantilever, then addition of such a species that binds specifically to the TAG can result in the production of a signal that is proportional to the TAG and therefore to the number of sugar molecules. An example is when the TAG is a biotin residue, commonly introduced by reaction with an active ester of biotin. Addition of an avidin-protein, when the TAG is a biotin residue, can result in signal that is readily detected and reported by the sensor. Other examples of sensors that can be used to detect the binding of second binding partners to immobilized TAGs include but are not limited to piezoelectric sensors, amperometric sensors, surface plasmon fluorescence spectroscopy sensors, dual polarization interferometry (DPI) sensors, wavelength-interrogated optical sensors (WIOSs), impedence sensors, optical waveguide grating coupler sensors, acoustic sensors and calorimetric sensors.

Once the monosaccharide has been attached to a TAG with spectroscopic properties, then said spectroscopic properties may be determined. The optical properties may be determined for sugars still immobilised on the solid support (such as for compound N of FIG. 3) or for sugars released to solution by a competing ligand (for example for compound P of FIG. 4). Depending on the nature of the TAG with spectroscopic properties, said properties may be determined using conventional methods, such as spectrometry. Thus the methods of the invention may comprise the step of detecting the TAG attached to the monosaccharide by spectrometry.

In one embodiment of the invention it is preferred that the TAG is a coloured moiety or a fluorescent moiety, which may even be detectable by visual inspection by eye. In this the embodiment the TAG may for example be any fluorescent moiety known to the skilled person, for example any of the fluorescent moieties described in The Handbook—*A Guide to Fluorescent Probes and Labeling Technologies* 10$^{th}$ edition available from Invitrogen—Molecular Probes. For example the TAG may be 6-TRITC or tetramethylrhodamine.

Further preferred boronic acid compounds suitable for use in the detection group of the present invention are disclosed in the following references:

"Boronic Acids: Preparation, Applications in Organic Synthesis and Medicine", ed. Dennis G. Hall, pub. Wiley-VCH, in particular in chapters 12 and 13 ("Boronic Acid-based receptors and sensors for saccharides" and "Biological and medicinal applications of boronic acids").

Yan et al., "Boronolectins and Fluorescent Boronolectins: An Examination of the Detailed Chemistry Issues Important for the Design", Medicinal Reseach Reviews, Vol. 25, No. 5, 490-520, 2005

Mulla et al., "3-Methoxycarbonyl-5-nitrophenyl boronic acid: high affinity diol recognition at neutral pH", Bioorganic & Medicinal Chemistry Letter 14 (2004) 25-27

Dowlut et al., "An Improved Class of Sugar-Binding Boronic Acids, Soluble and Capable of Complexing Glycosides in Neutral Water", J. Am. Chem. Soc. 2006, 128, 4226-7

Hoeg-Jensen., "Preparation and Screening of Diboronate Arrays for Identification of Carbohydrate Binders", QSAR Comb., Sci. 2004, 23

Boduroglu et al., "A colorimetric titration method for quantification of millimolar glucose in a pH 7.4 aqueous phosphate buffer", Bioorganic & Medicinal Chemistry Letter 15 (2005) 3974-3977

Davis et al., "Simple and Rapid Visual Sensing of Saccharides", Organic Letter, 1999 Vol. 1, No. 2, 331-334

He et al., "Chromophore Formation in Resorcinarene Solutions and the Visual detection of Mono- and Oligosaccharides", J. Am. Chem. Soc. 2003, 124, 5000-5009

Gray et al., "Specific sensing between inositol epimers by a bis(boronate)", Bioorganic & Medicinal Chemistry Letters 15 (2005) 5416-5418)

Capping and reduction: After binding of the terminal monosaccharide(s) to the capture group(s), the solid support coupled to the immobilised monosaccharide (such as compound G-L of FIG. 3) may still contain unreacted free capture groups and can be subjected to unique manipulations that increase the scope of its utility.

Thus, in one embodiment, a capping agent is bound to unbound capture groups before step (iv) of the method. For example, in one preferred embodiment of the invention, subsequent to immobilisation of the reducing sugar, unreacted capture groups are capped by a capping agent, under conditions where the bound monosaccharide is preferably not released form the capture group on the solid support. After capping the solid support will no longer comprise any free capture groups, but only capped groups of reduced reactivity towards e.g. electrophiles.

Any suitable capping agent known to one skilled in the art may be used in the present invention. For example, said capping agent is a capping group capable of reacting with a —NH$_2$ group. Examples of preferred capping agents are disclosed in FIG. 9.

Capping groups reacting with —NH$_2$ groups: In one preferred embodiment of the invention, subsequent to immobilisation of the monosaccharide, unreacted —NH$_2$ groups are capped by a capping agent, such as an acylating agents (e.g. acetic anhydride) or other nitrogen-reactive agents well known in the art, under conditions where the C=N bond of C does not react. After capping the solid support will no longer comprise any free amine groups, but only capped nitrogen atoms (N(H)CAP) of very low reactivity towards electrophiles. The product of the capping of compound C can for example contain an —R—N(H)CAP group, wherein the (H) may or may not be present depending on the structure of the CAP group.

For example, in specific embodiments if the C=N bond linking the sugar to the solid support is reduced to an —NH—, it can be a formally SP$^3$-hybridized nitrogen atom in the sequence R—NH—CH$_2$—. Specific reactions may be directed to this group, allowing specific and stoichimetric reactions at the monosaccharide.

Preferably the capping agent specifically reacts with the remaining —NH$_2$ groups, without substantially reacting with the C=N functionality. Such reagents are well known in the art an include common acylating agents used for amid bond formation, e.g. acetic anhydride, other alkanoic acid anhydrides, aromatic anhydrides (e.g. benzoic anhydride), cyclic anhydrides (e.g. succinic anhydride, phthalic anhydride), other active esters such as N-hydroxysuccinimide esters, pentafluorophenyl esters and a variety of active esters in common use in amide bond formation including in the solid phase synthesis of peptide bonds. The —NH$_2$ groups may alternatively be capped by adding the corresponding free acids and an in-situ activating agent such as DCC, in common use in peptide-bond formation thereby creating an active ester in situ. Other reagents known to be reactive towards —NH$_2$ groups can be used, such as alkyl isothiocyanates (R—NCS), aryl isothiocyantes (Ar—NCS), alkylating agents R-L (where L is a leaving group typically from the series Cl, Br, I, OS(O)$_2$R' where R' can be alkyl or aryl), Michael acceptors such as alpha-beta unsaturated carbonyl compounds (CHR=CH—CO— where R can be H, alkyl or aryl or substituted alkyl or aryl) or alpha-beta unsaturated sulfones (CHR=CHS(O)$_2$R' or Ar where R can be H, alkyl or aryl or substituted alkyl or aryl), sulfonating agents (such as RSO$_2$Cl) and derivatives thereof. In a similar manner, the —NH$_2$ groups can be capped by reaction with active esters of carbonates of the general formula RO—C(O) L, where L is described as above.

Reduction: In one preferred embodiment of the invention, the bond linking the monosaccharide to the linker (for example compound G or I of FIG. 1) is reduced using a reducing agent. However, in other embodiments of the invention the methods do not comprise such a reduction step. The bond may be reduced by a variety of well known reducing agents, as known by one skilled in the art. If the bond linking the monosaccharide to the linker is a C=N bond, preferably the reducing agent is capable of saturating the double bond while placing a hydrogen atom on the N.

Of special value are boranes or borohydrides comprising a BH bond, examples include NaBH$_4$, NaCNBH$_3$, and BH$_3$ complexes such as BH$_3$-pyridine, BH$_3$-dimethylsulfide or the like. Silanes with the structures R$_3$SiH can also be used, such as silanes comprising SiH bonds, as can hydrogen transfer agents such as diimides, or homogeneous hydrogenation catalysts or hydrogenation catalysts comprising a metal-H bond.

The reduction results in a reactive monosaccharide sugar containing the structure SugarCH—NH— preferably linked to a solid support via a linker. In general, if the monosaccharide sugar was an aldehyde, then reduction will result in a compound of the structure SugarCH$_2$—NH—. If the monosaccharide sugar was a ketone, then the reduction will result in a compound of the structure SugarCH—NH—.

In one embodiment of the invention, the capping step is carried out and the then reduction step is carried out. In another preferred implementation of the method, the order of the capping and reduction steps is reversed.

The reduction may in one embodiment be performed in situ, meaning that a reducing agent (such as NaCNBH$_3$) may be added to the solid support simultaneously with the monosaccharide. It is thus comprised within the present invention that the sample comprising the monosaccharide may be incubated with the solid support and the reducing agent simultaneously.

(iv) Allowing the Detection Agent to Bind the Monosaccharide

Stage (iv) of the method of the present invention comprises the step of allowing the detection agent to bind the monosaccharide.

Figure 3:
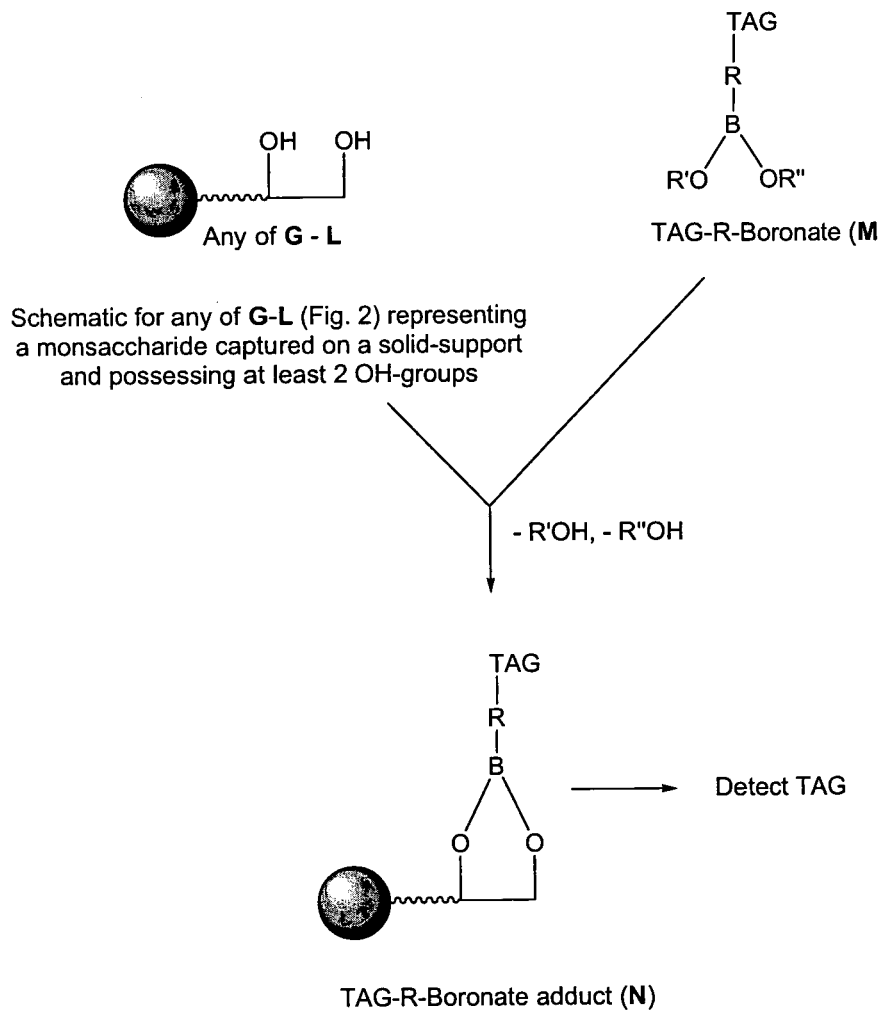
FIG. 3. Reaction of the detection agent TAG-R-Boronate (M) with the captured monosaccharide (any of G—L, FIG. 2) to form a covalent adduct N. The abbreviated schematic for any of G—L (FIG. 2) shows that the immobilized monosaccharide contains a diol that is capable of binding to the boron atom. Other binding groups, such as triols, amino-alcohols or a hydroxy-acids, are also possible. The TAG can be detected either directly, or indirectly through a perturbation of the solid support.

This reaction of the TAG-R-Boronate with the captured monosaccharide is exemplified in FIG. 3:—The captured monosaccharide bonded to the solid support (any of G-L) is contacted with a solution of a functionalized boronic acid of the general formula TAG-R-Boronate (M), where R is preferably aromatic or heteroaromatic. The "TAG" can be any moiety that permits the specific detection of the Tagged species, either directly—such as by using a fluorescent TAG—or indirectly—for example by measuring a mass change attributed to a heavy metal TAG. After incubation with any of G-L, the TAG-R-Boronate (M) will stay covalently attached to the monosaccharide-solid support (such as, for example via at least one OH-group) and optionally, the unbound TAG-R-Boronate can be washed away. This leaves a solid material referred to as TAG-R-Boronate-adduct (N). In the absence of attched Glycose, the TAG-R-Boronate will not remain attached to the solid support and will be washed away from the solid support that will then not have any attached TAG.

Optionally, the method according to the present invention comprises a further step after step (iv), wherein unbound detecting agent is removed, preferably by washing. Thus, in one embodiment the tagged immobilised terminal monosaccharide (e.g. compound N, FIG. 3) is washed prior to any further manipulations. Thus any amount of unbound TAG is removed. Washing may easily be accomplished because the tagged monosaccharide is immobilised on a solid support.

After washing, only covalent bound TAG will be present. Thus the amount of TAG will be correlatable to the amount of immobilised sugar. Accordingly, by determining the presence of TAG, the amount of immobilised sugar may be determined. If essentially all monosaccharide in a given sample was immobilised, the methods therefore in one aspect allow determining the amount of monosaccharide present in a sample.

The skilled person will readily be able to identify suitable washing conditions for a given tagged, monosaccahirde (e.g. compound N, FIG. 3). The washing may for example be done with a solvent selected from the group consisting of water, aqueous buffer, organic solvents and mixed aqueous and organic solvents. The solvent may also be any of the aforementioned comprising one or more additives such as salts, divalent metal cations, detergents, complexing agents including inclusion-complex-forming molecules such as cyclodextrins or calixarenes, chelating agents (for example EDTA), borates, boronates or silicates. Furthermore, the solvent may optionally comprise detergents and denaturing agents. The washing my be performed at any temperature, but preferably at temperatures in the range of 0-100° C.

(v) Detecting Detection Agent having Bound to the Monosaccharide

Stage (v) of the method of the present invention comprises the step of detecting detection agent having bound to the monosaccharide.

This detection step can allow conclusions to be drawn in relation to the identity of the terminal monosaccharide cleaved from the glycosylated substrate A, for example the detection step may allow identification of at least one of the terminal monosaccharide(s) on the glycosylated substrate. One preferred identification method is via indirect identification of the monosaccharide according to the specific detachment method used, for example if one uses a specific glycosidase in step (i) of the method, one can then infer the identity of the monosaccharide detached based on the specificity of the glycosidase used.

Many methods are known by one skilled in the art as suitable for use in detecting the detection agent. For example, the detecting step can be carried out by measuring absorbance or fluorescence. Thus, the detecting step can be carried out by using spectrometry, such as fluorospectrometry.

It is preferred that the analysis allows quantification of at least one of the monosaccharide(s) on the glycosylated substrate. Thus, the amount of TAG present on the TAG-R-Boronate adduct will indicate that amount of monosaccharide present, whose quantity can therefore be estimated using a standard curve of captured reference monosaccharide. For example, the quantification may be carried out by comparing the results obtained with standard curve obtained using different concentrations of a known reference sample.

In one embodiment of the invention, the TAG molecule is released from the solid support before quantification.

This release step is exemplified in FIG. 4:—wherein the soluble TAG-R-Boronate (P) is released back into solution from the TAG-R-Boronate adduct (N) by contacting it with a solution of a cleaving agent comprising a competing ligand (O) The TAG-R-Boronate (P) released into solution can then be estimated by solution methods that detect the TAG, such as spectroscopy. The TAG will no longer be detectable on the residual solid-support which will have the structure according to any of G-L.

The cleaving agent (O) can for example be a soluble compound that competes with the immobilized monosaccharide and makes covalent bonds to the boronate moiety. Such compounds include polyalcohols like glycerol or glucitol, or amino-alcohols like diethanolamine. Under certain conditions, water or alcohols may act as competing ligands.

In one embodiment of the invention a predetermined amount of a reference standard is added to the sample comprising the glycosylated substrate. This may facilitate quantification of any released monosaccharide after immobilisation, and/or validate the efficiency of the capture-beads in a complex sample. The reference standard can for example be a compound capable of reacting with —$NH_2$. Preferably the reference standard is an aldehyde or a ketone, more preferably a sugar, such as a monosaccharide.

The present invention surprisingly discloses a high affinity between boranate and immobilised terminal monosaccharides. Accordingly, the methods of the invention are sufficiently sensitive in order for relatively insensitive methods to be used for detection. Accordingly, surprisingly in one preferred embodiment of the invention the detection may be visual detection by eye. Visual detection by eye may for example be performed as described in Example 1 and disclosed in FIG. 13 herein.

Repeating the Method

The method described herein may advantageously be repeated at least once, such as 1, 2, 3, 4, 5, 6, 7, 8, 9, 10 or more times. This can for example be advantageous should one wish to use the methods described herein for monosaccharide sequencing of a glycosylated molecule, such as a polysaccharide. The repetitions of any of the methods disclosed herein may be carried out in parallel on different samples of glycosylated substrates and/or using different methods for detaching the monosaccharide(s) from said glycosylated substrate(s). For example, one may repeat the method using one or more different specific glycosidases (optionally on parallel samples), in order to indirectly determine the identity of the relevant monosaccharides through the specificity of the glycosidase used.

Thus, the present invention provides in one aspect a method for oligosaccharide or polysaccharide sequencing, comprising subjecting a polysaccharide or molecule comprising a polysaccharide to any of the methods disclosed herein.

Method of Diagnosis of a Disease

The methods of the present invention may be used to identify particular glycosylation patterns associated with certain pathological conditions, thus in a further aspect of the present invention is disclosed a method of diagnosis of a disease associated with abnormal glycoprotein glycosylation, comprising subjecting a sample of glycoproteins obtained from a patient to any of the methods as disclosed herein. Identification of one or more of the monosaccharides on the glycosylated substrate of interest can for example allow diagnosis of a specific glycoylation pattern associated with a particular disease class. Preferred diseases associated with an abnormal glycosylation patterns include, but are not restricted to, Carbohydrate-Deficient Glycosylation Syndromes (CDGS), CDGS I, CDGS II, CDGS III, CDGS IV, neuronal diseases, diabetes, Tay-Sachs disease and cancers.

Method for Monitoring for Bacterial Contamination of Products

The method of the present invention may also be used advantageously to assay for bacterial contamination of products. Thus, in another aspect of the present invention is provided a method for monitoring for bacterial contamination of products, such as food, beverages or pharmaceutical products, comprising subjecting a sample of said product to one of the methods disclosed herein. This may be particularly advantageous for e.g. checking the quality of therapeutic glycosylated proteins, as disclosed in e.g. Sinclair et al., "Glycoengineering: the Effect of Glycosylation on the Properties of Therapeutic proteins". Thus, in one preferred embodiment of the present invention is provided a method for characterising therapeutic glycosylated proteins, comprising carrying out any of the methods describe herein.

Covalent Adduct

When carrying out the method of the present invention, a covalent adduct is formed between the monosaccharide and the detection agent, as disclosed herein. Thus, in one aspect of the present invention is disclosed a covalent adduct formed between a monosaccharide captured on the solid phase, such as any of the monosaccharides disclosed herein, and a detection agent with formula X:

TAG-R-Boronate;

such as any of the detection agents disclosed herein.

Preferably, the covalent adduct is covalently bound to a capture group on a solid support.

Fluorescent Compounds

When carrying out the method of the present invention, it is preferred that fluorescent compounds are used as the TAG component of the detection agent. Thus, in one aspect of the present invention is disclosed novel fluorescent compounds useful as TAG compounds, which can be used to produce the detection agents used in the present invention. Any of the fluorescent compounds disclosed herein may be used: two preferred fluorescent compounds have the following structures: fluorescent hydroxymethyl-boronate 1 (shown in FIG. 11) and fluorescent nitro-boronate 2 (shown in FIG. 12)

Methods for manufacture of any of the fluorescent compounds disclosed herein are well-known to those skilled in the art, for example as disclosed in e.g. "Boronic Acids: Preparation, Applications in Organic Synthesis and Medicine", edited by Dennis G. Hall, pub. Wiley-VCH Verlag GmbH & Co. KGaA, Weinheim, in particular chapter 1: "Structure, Properties, and Preparation of Boronic Acid Derivatives. Overview of Their Reactions and Applications".

Kit of Parts

In another aspect of the present invention is disclosed a kit of parts suitable for using in the methods of the present invention, said kit of parts comprising at least one solid support (such as any of the solid supports disclosed herein), at least one capture group (such as any of the capture groups disclosed herein), and one or more detection agents, such as any of the detection agents disclosed herein. Said kit of parts may also further comprise at least one specific glycosidase and/or a sample of glycosylated substrate, preferably for use as a positive control in quantitative or qualitative assays.

EXAMPLES

The following are illustrative examples of the methods of the invention and should not be considered as limiting for the invention.
Abreviations used:
AMP-CPG: aminopropyl controlled pore glass
DMF: dimethylformamide
DIPEA: diisopropylethylamine
TBTU: N,N,N',N'-tetramethyl-O-(benzotriazol-1-yl)uronium tetrafluoroborate
DCM: dichloromethane
DBU: 1,8-diazabicyclo[5.4.0]undec-7-ene
6-TRITC: 6-tetramethylrhodamine isothiocyante
ES-MS: electrospray mass spectrum
EDC: N-ethyl-N'-(3-dimethylaminopropyl)carbodiimide
BSA: bovine serum albumin
rt: room temperature Example 1

Synthesis of Capture Beads (FIG. 10)

Aminopropyl controlled pore glass (AMP-CPG, Millipore Prod. No. AMP 1400B) (500 mg, loading of amino groups, ca 50 μmol/g) was washed with DMF (3×2 mL), 50% DIPEA in DMF (3×2 mL) and DMF (3×2 mL). The beads were then treated with a mixture of the hydroxylamine linker 3 (45 mg, 100 μmol), TBTU (25 mg, 75 μmol) and DIPEA (13 μL, 75 μmol) in DMF (2 mL) for 2 h at rt. The beads were washed with DMF (3×2 mL) and DCM (3×2 mL). Unreacted amino groups were capped by treating the beads with 50% $Ac_2O$ in pyridine (2 mL) for 15 min at rt. Silanol groups (on the glass surface) were capped by treating the beads with 5% dichlorodimethylsilane in toluene (2 mL) for 30 min at rt, followed by 10 min incubation in dry MeOH. The silanol capping was repeated. The beads were washed with MeOH, DMF and DCM. A small portion of the beads was removed and the loading was determined to be ca 35 μmol/g based on the absorbance of the Fmoc group released on treatment with 10% DBU in DMF, by comparison with a standard curve prepared using known concentrations of cleaved Fmoc group.

Synthesis of fluorescent hydroxymethyl-boronate 1 (FIG. 11)

6-TRITC (4, 7.4 mg, 17 μmol) was added to a solution of 5-amino-2-hydroxymethyl phenyl boronic acid (5, Combi-Blocks Prod. No. BB-2043, 3.1 mg, 17 μmol) in 0.1 M $NaHCO_3/Na_2CO_3$ buffer pH 9 (1 mL) and DMF (1 mL). The mixture was stirred over night at rt in the dark. The mixture was concentrated under vacuum and the crude product was dissolved in water, adsorbed on a Sep-Pak cartridge (C-18) which was washed with $H_2O$. Elution with 30-50% MeCN in $H_2O$ (containing 10% 0.1 M HCl) gave 1 as a purple solid (6.3 mg, 64%). ES-MS, m/z found 593.2 ([MH]$^+$ calcd 593.2).

Preparation of ethylenediamine extended lissamine 7 (FIG. 12)

To a solution of ethylenediamine (232 μL, 3.47 mmol) in DCM (5 mL) was added Lissamine rhodamine B sulfonylchloride (6, mixture of 5/6 isomers, 100 mg, 0.17 mmol) in one portion. The mixture was stirred over night at rt in the dark. The mixture was concentrated under vacuum and the crude product was purified by adsorption on a Sep-Pak cartridge (C-18) which was washed with $H_2O$. Elution with 30% MeCN in $H_2O$ (containing 10% 0.1 M HCl) gave 7 as a purple solid that was used without further characterisation.

Synthesis of fluorescent nitro-boronate 2 (FIG. 12)

To a suspension of (3-carboxy-5-nitrophenyl)boronic acid (8, Combi-Blocks Prod. No. BB2476, 1.76 mg, 8.33 μmol), $HOBt.H_2O$ (1.13 mg, 8.33 μmol), EDC.HCl (1.60 mg, 8.33 μmol) and DIPEA (1.45 μL, 8.33 μmol) in dry DCM (1 mL) was added 7 (5.00 mg, 8.33 μmol). The mixture was stirred for 2 h at rt in the dark. More DCM (5 mL) was added and the mixture was washed with sat. $NaHCO_3$ and 0.1 M HCl. The organic phase was concentrated under vacuum and the crude product was purified by dry column vacuum chromatography using 50% MeOH in $CHCl_3$ (containing 1% 0.1 M HCl). The fractions containing the product were concentrated and redissolved in DCM (5 mL) and washed with half sat. aq. $NaHCO_3$. The organic phase was dried ($Na_2SO_4$), filtered and concentrated giving product 2 as a purple solid (4.7 mg, 70%). ES-MS m/z found 816.3 ([MNa]$^+$, calcd 816.2)

Preparation of bovine serum albumin (BSA) for enzyme digestion

BSA (5×2 mg/mL ampules, Pierce #23209) was dialyzed twice against water (5 L), and concentrated to 20 mg/mL in a centricon-30 ultrafiltration tube.

Preparation of β-galactosidase for glycoprotein digestion

A centricon-30 ultrafiltration tube was preconditioned by washing with water (2 mL), then spun for 8 min at rt to clean the membrane. Commercial β-galactosidase from bovine testes (Sigma, G4142) was dissolved in buffer (0.1 M citrate/phosphate, pH 5.0) and 2 mL was added to the Centricon tube. The tube was spun at 4000×g until 50 μL remained. The filtrate was discarded, and the retentate made up to 2 mL with buffer. This was centrifuged again until 50 μL remained. The entire process of discarding the filtrate, adding buffer to 2 mL and centrifuging was repeated 4 more times. After discarding the final filtrate, the tube was inverted and spun for 2 min at 1000×g, yielding a solution of the enzyme in buffer ready for use.

Digestion of Proteins and Glycoprotein Samples with Beta-Galactosidase

Solutions of 10 mg/mL of the proteins (fetuin (Sigma F3004), asialo-fetuin (Sigma A4781) and the dialyzed BSA described above, were incubated in buffer at 37° C. overnight, both with and without added beta-galactosidase (0.23 U/mL). Six YM-10 ultrafiltration tubes were prepared by washing the membranes with pure water (500 μL, centrifuging 30 min at 14,000×g) to remove any glycerol from the membranes, removing the retentate by shaking, and replacing the receiving tube with a fresh receiving tube. Then 200 μL of each of the six incubation solutions was added to a freshly prepared YM-10 tube which was centrifuged for 45 min at 14,000×g. The filtrates from each tube were used for the capture experiments, and are referred to as Fet− (for the solution of Fetuin without added galactosidase), Fet+ (for the solution of Fetuin with added galactosidase), AFet− (for the solution of asialo-fetuin without added galactosidase), AFet+ (for the solution of asialo-fetuin with added galactosidase), BSA− (for the solution of BSA without added galactosidase) and BSA+ (for the solution of BSA with added galactosidase).

Capture of Galactose on Capture-Beads.

All manipulations were performed under a stream of argon. Beads (10 mg, 0.35 μmol of Fmoc-protected capture groups, FIG. 10) were placed in each of eight glass test tubes and each was Fmoc-deprotected by treatment with 10% DBU in DMF (200 μL) for 20 min. The cleaving solution was decanted and the beads were washed with DMF (3×2 mL) and 0.1 M citrate/phosphate buffer pH 5 (3×1 mL) with decanting of each of the washes.

To one tube each of the resulting hydroxylamine Capture Beads (FIG. 10) was added 50 μL of Fet−, Fet+, AFet−, AFet+, BSA−, BSA+, galactose (2 mM) in buffer (referred to as Gal-std), and buffer alone (referred to as Blank). More buffer (50 μL) was added to each tube. The tubes were stoppered and incubated overnight at 60° C. in a heating block. After cooling to rt, remaining capture groups were capped by adding 50% acetic anhydride in MeOH and shaking gently for 20 min.

The remaining manipulations were no longer performed under argon. The beads from each tube were transferred to a plastic syringe equipped with a Teflon frit, and washed by aspiration with buffer (3×0.5 mL), H$_2$O (3×0.5 mL), MeOH (3×0.5 mL), H$_2$O (3×0.5 mL), 5% DIPEA in DMF (0.5 mL), DMF (3×0.5 mL), H$_2$O (3×0.5 mL) and MeOH (3×0.5 mL). A portion of each batch of beads was dried under vacuum.

Staining and visual detection of captured galactose on treated Capture Beads after treatment with fluorescent hydroxymethyl-boronate 1 (FIG. 13)

The dried capture beads (2 mg) described above that had been exposed to each of Fet−, Fet+, AFet−, AFet+, BSA−, BSA+, Gal-std and Blank solutions, were washed with DMF (1×0.5 mL) and treated with a mixture of 0.5 mM 1 (FIG. 11) in DMF (100 μL) and 0.1 M carbonate buffer pH 9 (100 μL). The resulting samples were shaken gently for 1 h at rt. The beads were washed with DMF (3×0.5 mL), 0.1 M carbonate buffer pH 9 (1×0.5 mL), H$_2$O (1×0.5 mL), DMF (3×0.5 mL), DCM (3×0.5 mL). Portions of the beads were transferred to small glass vials and photographed with a hand-held digital camera (FIG. 13, top panel).

Release of fluorescent boronate from stained beads (FIG. 13)

A solution of glycerol/MeOH/H$_2$O (1:2:2, v/v/v, 100 μL) was added to the each of the tubes containing beads shown in the top panel of FIG. 13. The samples were shaken gently for 1 h. The supernatants were removed from each tube and transferred to fresh plastic Eppendorf tubes. The supernatants from the tubes designated AFet+ and Gal-std were bright red while the supernatants from the other beads were clear (FIG. 13, bottom panel). Washing of the residual beads once more with glycerol/MeOH/H$_2$O (1:2:2, v/v/v, 100 μL) left the beads designated AFet+ and Gal-std white again, indistinguishable from the others (FIG. 13, middle panel).

(These Examples exemplify use of compound 1 shown in FIG. 11; Compound 2 shown in FIG. 12 was found to be equally effective to Compound 1 for the staining and detection of galactose captured on Capture Beads, and was equally efficiently released on treatment with glycerol.)

We claim:

1. A method for analyzing a terminal monosaccharide on a glycosylated substrate, comprising
   (i) detaching said monosaccharide from said glycosylated substrate by contacting with an exoglucosidase;
   (ii) allowing said detached monosaccharide to covalently bind to a capture group on a solid support;
   (iii) incubating said covalently bound monosaccharide with a detection agent of formula X:
   TAG-R-Boronate (Formula X)
   wherein TAG=a tag moiety capable of being detected
   R=organic moiety
   Boronate=a boronic acid moiety or ester thereof,
   said boronate being attached to a carbon atom comprised in said R group;
   (iv) allowing the detection agent to bind to the monosaccharide; and
   (v) detecting, directly or indirectly, the detection agent that is bound to the monosaccharide.

2. The method according to claim 1, further comprising removing the unbound detection agent after step (iv).

3. The method according to claim 1, wherein said capture group is attached to the solid support via a linker group.

4. The method according to claim 1, further comprising capping the unbound capture groups with a capping agent before step (iv).

5. The method according to claim 1, wherein the glycosylated substrate to be analysed is comprised within a sample, and wherein said method additionally comprises removing components of said sample by size exclusion, ultrafiltration or dialysis.

6. A method for polysaccharide sequencing, comprising
   (i) detaching a monosaccharide from said polysaccharide by contacting with an exoglucosidase;
   (ii) allowing said detached monosaccharide to covalently bind to a capture group on a solid support;
   (iii) incubating said covalently bound monosaccharide with a detection agent of formula X:
   TAG-R-Boronate (Formula X)
   wherein TAG=a tag moiety capable of being detected
   R=organic moiety
   Boronate=a boronic acid moiety or ester thereof,
   said boronate being attached to a carbon atom comprised in said R group;
   (iv) allowing the detection agent to bind to the monosaccharide; and
   (v) detecting, directly or indirectly, the detection agent that is bound to the monosaccharide.

7. The method according to claim 6, comprising employing a plurality of specific glycosidases, wherein the identity of the monosaccharide is determined through the specificity of the glycosidase.

8. A method of diagnosing a disease associated with abnormal glycoprotein or glycolipid glycosylation, comprising subjecting a patient sample comprising said glycosylated glycoprotein or glycolipid substrate to a method comprising
   (i) detaching a monosaccharide from said glycosylated glycoprotein or glycolipid by contacting with an exoglucosidase;
   (ii) allowing said detached monosaccharide to covalently bind to a capture group on a solid support;

(iii) incubating said covalently bound monosaccharide with a detection agent of formula X:
TAG-R-Boronate (Formula X)
wherein TAG=a tag moiety capable of being detected
R=organic moiety
Boronate=a boronic acid moiety or ester thereof,
said boronate being attached to a carbon atom comprised in said R group;
(iv) allowing the detection agent to bind to the monosaccharide; and
(v) detecting, directly or indirectly, the detection agent that is bound to the monosaccharide, wherein identification of one or more monosaccharides in the glycoprotein or glycolipid substrate present in said sample is diagnostically correlated with a specific glycoylation pattern associated with a particular disease.

9. The method according to claim 8, wherein the disease is carbohydrate-deficient glycosylation syndrome (CDGS) I (CDGS I), CDGS II, CDGS III, CDGS IV, a neuronal disease, diabetes, Tay-Sachs disease or a cancer.

10. A method for monitoring bacterial contamination of a product comprising detecting one or more sugar in the cell surface of said bacteria via a method comprising (i) detaching a monosaccharide from said cell-surface sugar by contacting with an exoglucosidase;
(ii) allowing said detached monosaccharide to covalently bind to a capture group on a solid support;
(iii) incubating said covalently bound monosaccharide with a detection agent of formula X:
TAG-R-Boronate (Formula X)
wherein TAG=a tag moiety capable of being detected
R=organic moiety
Boronate=a boronic acid moiety or ester thereof,
said boronate being attached to a carbon atom comprised in said R group;
(iv) allowing the detection agent to bind to the monosaccharide; and
(v) detecting, directly or indirectly, the detection agent that is bound to the monosaccharide,
wherein identification of one or more monosaccharides in the product is indicative of said bacterial contamination.

* * * * *